US007442840B2

(12) United States Patent
Elia et al.

(10) Patent No.: US 7,442,840 B2
(45) Date of Patent: Oct. 28, 2008

(54) SYNTHESIS OF SEVERELY STERICALLY HINDERED AMINO-ETHER ALCOHOLS AND DIAMINOPOLYALKENYL ETHERS USING A HIGH ACTIVITY POWDER CATALYST

(75) Inventors: Christine Nicole Elia, Bridgewater, NJ (US); Michael Siskin, Randolph, NJ (US); Michael Charles Kerby, Center Valley, PA (US); Adeana Richelle Bishop, Baton Rouge, LA (US); Edmund John Mozeleski, Califon, NJ (US); Andrzej Malek, Baton Rouge, LA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/587,205

(22) PCT Filed: Feb. 1, 2005

(86) PCT No.: PCT/US2005/003062

§ 371 (c)(1),
(2), (4) Date: May 4, 2007

(87) PCT Pub. No.: WO2005/081778

PCT Pub. Date: Sep. 9, 2005

(65) Prior Publication Data

US 2008/0058553 A1    Mar. 6, 2008

Related U.S. Application Data

(60) Provisional application No. 60/545,119, filed on Feb. 17, 2004.

(51) Int. Cl.
*C07C 209/16* (2006.01)

(52) U.S. Cl. ........................ 564/447; 564/474; 564/480

(58) Field of Classification Search .................. 564/447, 564/474, 480
See application file for complete search history.

(56) References Cited

U.S. PATENT DOCUMENTS

| 4,112,052 A | 9/1978 | Sartori et al. | 423/228 |
|---|---|---|---|
| 4,405,585 A | 9/1983 | Sartori et al. | 423/228 |
| 4,417,075 A | 11/1983 | Stogryn | 564/505 |
| 4,487,967 A | 12/1984 | Stogryn et al. | 564/474 |
| 4,508,692 A | 4/1985 | Savage et al. | 423/228 |
| 4,618,481 A | 10/1986 | Heinzelmann et al. | 423/228 |
| 4,665,195 A * | 5/1987 | Stogryn et al. | 548/523 |
| 4,892,674 A | 1/1990 | Ho et al. | 252/189 |
| 4,894,178 A | 1/1990 | Ho et al. | 252/189 |
| 4,961,873 A | 10/1990 | Ho et al. | 252/189 |
| 5,098,604 A | 3/1992 | Brouard et al. | 252/311.5 |
| 5,098,684 A | 3/1992 | Kresge et al. | 423/277 |
| 5,102,643 A | 4/1992 | Kresge et al. | 423/328 |
| 5,227,353 A | 7/1993 | Apelian et al. | 502/74 |
| 5,250,282 A | 10/1993 | Kresge et al. | 423/705 |
| 5,573,657 A | 11/1996 | Degnan et al. | 208/144 |
| 5,936,126 A | 8/1999 | Rühl et al. | 564/451 |
| 5,951,962 A | 9/1999 | Müller et al. | 423/702 |
| 6,238,701 B1 | 5/2001 | Müller et al. | 424/489 |
| 6,248,924 B1 | 6/2001 | Rühl et al. | 564/450 |
| 6,284,917 B1 | 9/2001 | Brunner et al. | 560/127 |

FOREIGN PATENT DOCUMENTS

| WO | WO 2004/045767 | 3/2004 |
|---|---|---|
| WO | WO 2004/046076 | 3/2004 |
| WO | WO 2005/082834 | 9/2005 |

OTHER PUBLICATIONS

Winsor, P.A., "Binary and Multicomponent Solutions of Amphiphilic Compounds", Chemical Reviews, vol. 68, No. 1, Jan. 25, 1968, pp. 1-40.
Ulrike Ciesla et al, "Ordered mesoporous materials", Microporous and Mesoporous Materials, 27 (1999), pp. 131-149.

* cited by examiner

*Primary Examiner*—Peter G O'Sullivan
(74) *Attorney, Agent, or Firm*—Paul E. Purwin

(57) ABSTRACT

The present invention relates to a process for preparing severely sterically hindered secondary amine ether alcohols and diamine polyalkenyl ethers by reacting a primary amino compound with a polyalkenylether glycol in the presence of a high activity nickel powder hydrogenation catalyst which is marked by high conversion of reactants and increased selectivity to desired final product.

14 Claims, 6 Drawing Sheets

SYNTHESIS OF SEVERELY STERICALLY HINDERED AMINO-ETHER ALCOHOLS AND DIAMINOPOLYALKENYL ETHERS USING A HIGH ACTIVITY POWDER CATALYST

This application is the U.S. National Phase filing of PCT Application No. PCT/US2005/003062 filed Feb. 1, 2005, which claims priority to U.S. Provisional Patent Application No. 60/545,119 filed Feb. 17, 2004.

FIELD OF THE INVENTION

The present invention relates to the catalytic synthesis of severely sterically hindered secondary amino-ether alcohols and diaminopolyalkenyl ethers from primary amino compounds and polyalkenylether glycol.

DESCRIPTION OF THE RELATED ART

The catalytic production of severely sterically hindered amino ether alcohols is already established in the literature. Such severely sterically hindered amino-ether alcohols are made by reacting a primary amino compound, such as tertiary-butyl amine (TBA), with a polyalkenyl ether glycol, such as diethylene glycol (DEG), in the presence of a catalytically effective amount of a Group VIII metal containing hydrogenation catalyst at elevated temperature and pressure, such as about 160° C. to about 425° C. and about 50 to about 3,000 psig, as described in U.S. Pat. 4,487,967. The patent describes both supported and unsupported catalysts. Catalysts described in that patent include: Ni/AlO₃—SiO₂ [Harshaw Ni 5132P], Ni/kieselguhr, Ni/proprietary support [Harshaw Ni 3250T], Pt/graphite, Pt/carbon, Pt/Al₂O₃, Raney Nickel, Nickel [93.4 Ni-612 Al(B-113W)], Nickel [92.7 Ni-6.9 Al (B-133RZ)]. The reaction of tertiary-butyl amine with diethylene glycol produces ethoxyethanol-tertiary-butyl amine, known as EETB. EETB is useful in gas treating processes for the selective removal of H₂S from gas streams containing mixtures of H₂S and CO₂. The use of such severely sterically hindered amino-ether alcohols in such a separation process is described in U.S. Pat. Nos. 4,894,178, 4,405,585, 4,508,692, 4,618,481, 4,112,052, 4,961,873, 4,892,674, and 4,417,075.

There is a need, however, for a new process for the production of severely sterically hindered amino-ether alcohols which produce lower levels of undesirable by-products, have higher levels of conversion of the glycol reactant and improved selectivity for the desired product at such higher levels of conversion. It is an object of the present invention to provide a new catalytic process for the production of severely sterically hindered amino-ether alcohols using a class of catalyst which is marked by a high level of conversion of starting material and improved selectivity for the desired end-product.

SUMMARY OF THE INVENTION

Figure 1:
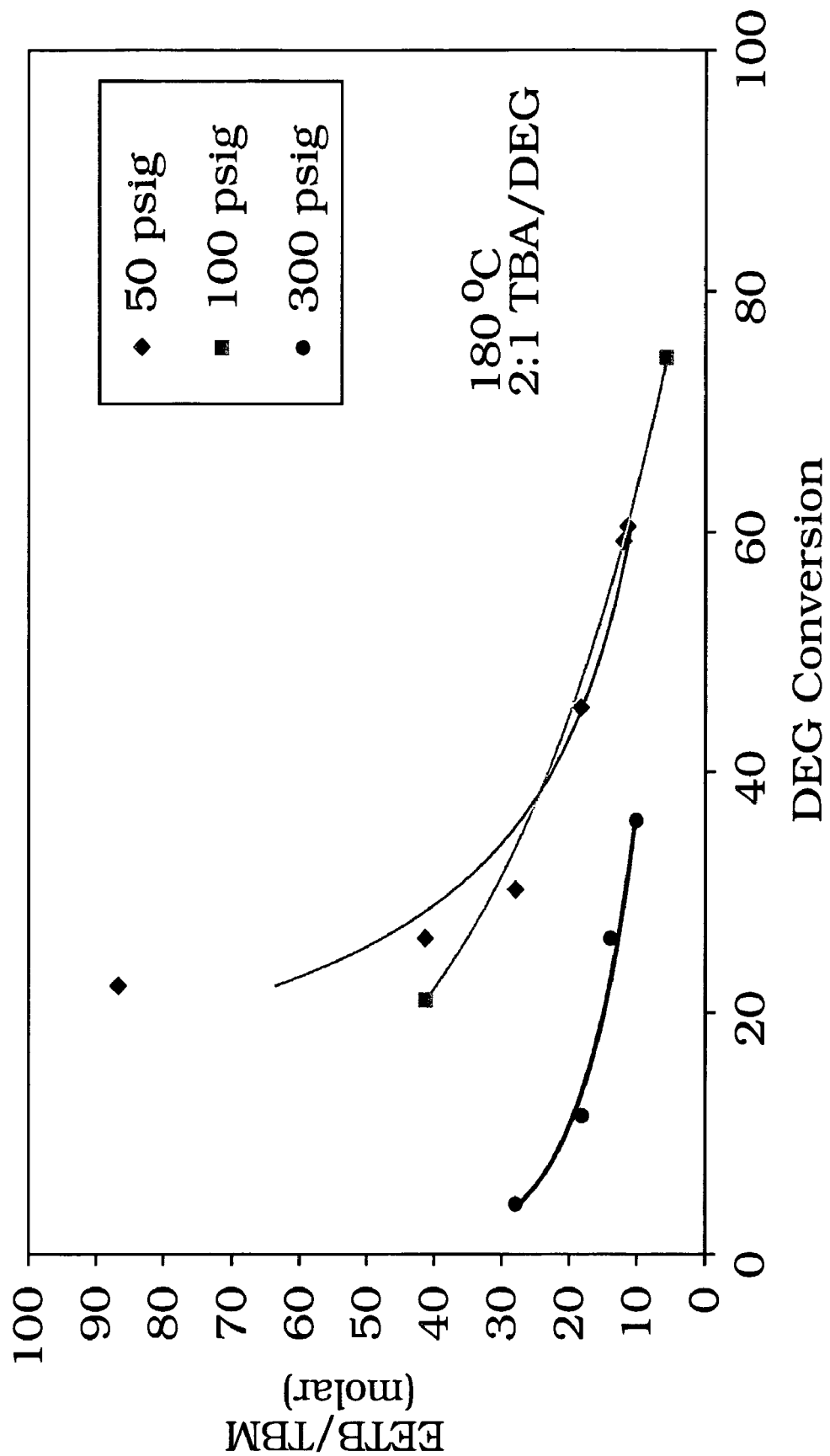
FIG. 1 is a plot of the level of DEG conversion versus the EETB/TBM ratio for three runs where the hydrogen pressure was 50 psig, 100 psig and 300 psig, respectively. TBM is an undesirable side product (N-tertiary-butylmorpholine).

The present invention is directed to a process for the production of severely sterically hindered amino-ether alcohols, diamine polyalkenyl ethers, and mixtures thereof, preferably severely sterically hindered aminoether alcohols, by the reaction of an alkyl substituted primary amino compound with a polyalkenyl ether glycol over a catalyst comprising a high activity metal powder catalyst. The catalytically active metal component comprises at least one metal of the transition group VIII of the Periodic Table, excluding platinum and palladium, (e.g., iron, cobalt, nickel, ruthenium, rhodium, osmium, iridium) either alone or together with at least one additional metal selected from the group consisting of transition Group 1B (e.g. copper) Group IIA (e.g., magnesium) and mixtures thereof. Preferably the catalyst comprises nickel and cobalt, more preferably nickel, most preferably powdered nickel. The metal loaded catalyst is characterized by having a BET surface area in the range of about 50 to about 1200 m²/g, and a micropore volume above 0.05 cm³/g. The catalyst comprising metal on support comprises about 2.5 to 80% reduced metal component, preferably about 10 to about 65% reduced metal based on the total weight of the reduced catalyst. In the case of nickel, it is preferred that the amount of reduced metal be at least 10%, preferable at least 12%, more preferably at least 14%. The metal loaded catalyst exhibits a pore size distribution, when normalized for pores of 19.99 nm and less, of about 30% or more of pores of up to 4.99 nm, preferably 35-100% of pores of up to 4.99 nm, more preferably about 40-100% of pores up to 4.99 nm, and pores of 5.0 up to 19.99 nm constituting the balance, preferably 30% or less of pores of 5 to up to 9.99 nm, preferably 0-25% of pores of 5 to up to 9.99 nm, the pores of 10 to up to 20 nm constituting the balance.

The process comprises the batch or continuous production of severely sterically hindered amino ether alcohols, diamino polyalkenyl ethers, and mixtures thereof, by reacting (a) an alkyl substituted primary amino compound of the general formula

wherein R¹ is selected from the group consisting of secondary-and tertiary-alkyl radicals having 3 to 8 carbon atoms, cycloalkyl radicals having 3 to 8 carbon atoms, and mixtures thereof, preferably secondary or tertiary alkyl radicals having 4 to 6 carbon atoms, more preferably tertiary alkyl radicals having 4 to 6 carbon atoms, with (b) a polyalkenyl ether glycol of the general formula

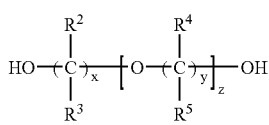

wherein $R^2$, $R^3$, $R^4$ and $R^5$ are each independently selected from the group consisting of hydrogen, $C_1$-$C_4$ alkyl radicals, and $C_3$-$C_8$ cycloalkyl radicals, with the proviso that if the carbon atom of $R^1$ directly attached to the nitrogen atom is a secondary alkyl radical, at least one of $R^2$ and $R^3$ directly bonded to the carbon which is bonded to the hydroxyl group is an alkyl or cycloalkyl radical, x and y are each positive integers independently ranging from 2 to 4, and z is from 1 to 10. The mole ratio of amino compound to polyalkenyl ether glycol is in the range of about 10:1 to 0.5:1, preferably about 5:1 to 1:1, more preferably about 3:1 to 1:1, provided that the ratio is less than 2:1 when z is greater than 1. When z is 1 the ratio is most preferably between from about 3:1 to about 2:1.

Preferably $R^1$ is an alkyl radical having 4 to 6 carbon atoms, $R^2$ and $R^3$ are hydrogen, x and y are 2 and z is 1. Typical secondary or tertiary alkyl primary amines useful in the present process include isopropylamine, tertiary-butyl amine, 1-methyl-1-ethyl propyl amine, and tertiary-amyl amine. Polyalkenyl ether glycols include diethylene glycol, triethylene glycol, di-isopropylene glycol. Most preferably $R^1$ is tertiary-butyl, $R^2$, $R^3$, $R^4$ and $R^5$ are hydrogen, x and y are 2 and z is 1. When the reactants are so defined the compound produced is predominantly ethoxyethanol tertiary-butyl amine (EETB) with a minor quantity, if any, of co-produced bis(tertiary-butyl amine ethoxy) ethane (a diamino polyalkenyl ether).

The reaction of the primary amine compound with the polyalkenyl ether glycol is conducted at an initial hydrogen pressure at room temperature of from about zero to about 300 psig, preferably about 50 to about 200 psig, more preferably about 50 to about 150 psig, at a temperature of about 150° C. to 350° C., preferably about 160° C. to about 300° C., more preferably about 180° C. to about 225° C., at a total reactor reaction pressure at operating temperature of about 50 to 1500 psig, preferably about 50 to 1000 psig, more preferably about 50 to 500 psig. The time the reaction is run is important in terms of by-product formation. The actual time required in a particular reaction will vary and is dependent upon the specific reactants, temperature and pressure used, as well as the size of the batch being processed. Long reaction times generally favor undesirable by-product formation, i.e. the increased production of N-tertiary-butyl morpholine (TBM) as do higher reaction temperatures. In general, the reaction is run for a time ranging from about 0.5 to 24 hours, preferably about 1 to 12 hours, more preferably about 1 to 8 hours.

In the present process, the concentration of the catalyst is that which is sufficient to promote the catalytic conversion of the primary amine and the polyalkenyl ether glycol into the severely sterically hindered amino-ether alcohol, diaminopolyalkenyl ether, and mixtures thereof. Thus, the amount of catalyst present with respect to the total amount of reactant will generally range from about 0.001 to about 10 wt %, preferably about 0.001 to about 8 wt %, more preferably about 0.01 to about 5 wt %, most preferably about 0.1 to about 1 wt % catalyst based on the weight of the total reactant charge.

The reaction may be conducted in any reactor vessel capable of withstanding the pressures and temperatures necessary to carry out the process. The reactants can be mixed with the catalyst and reacted in a batch process. The catalyst in the reactor can be slurried in the reaction mixture or encased in a basket. Alternatively, the reactants can be passed over a fixed bed of the catalyst, either co-currently or counter-currently. Other reactors suitable for use include moving bed reactors and continuously stirred reactors. For example, in a continuous stirred reactor the catalyst is circulated and the reactants and reaction products are passed through the reaction vessel at a controlled rate.

The reaction can be carried out in the absence of any added solvent, the liquid reactants functioning as the liquid reaction medium to facilitate reaction. However, an inert solvent can be included in the reaction medium.

Typical solvents include linear or cyclic ethers or hydrocarbon-containing compound in which the reactants will dissolve, or in excess secondary or tertiary alkyl amine reagent. The solvent should be relatively low molecular weight to facilitate removal from the product of the reaction. The amount of the solvent may vary, but will generally range from about 10 to 50 wt %, preferably from about 15 to 30 wt % based on the weight of the reactants used. Examples of typical solvents include dimethylether, ethylene glycol dimethyl ether, toluene, tetrahydrofuran. Because excess amine reagent can function as solvent, excess isopropyl amine, tertiary-butyl amine, tertiary-amyl amine and the like can be present in the reactor functioning as both reactant and solvent. The preferred solvents include tetrahydrofuran, dimethylether, ethylene glycol dimethylether and toluene.

The catalyst comprises a reduced metal component deposited on a porous support. The catalytic component is provided by a metal or combination of metals. The catalytic metals that may be used are preferably one or more metals of Transition Group VIII of the Periodic Table, excluding platinum and palladium, alone or in combination with one or more metals of Group 1B and may also be combined with one or more metals from main Group IIA. Preferably, the catalytically active metal component is selected from the group consisting of nickel, iron, cobalt, osmium, iridium, ruthenium, rhodium, and mixtures thereof, more preferably nickel and cobalt, most preferably nickel, which can be in combination with an additional catalytic component selected from the group consisting of copper, silver, gold, and mixtures thereof, preferably copper, and may further contain an additional metal selected from the group consisting of beryllium, magnesium, calcium, strontium, barium, and mixtures thereof, preferably magnesium, calcium, and mixtures thereof, more preferably magnesium. Preferred the catalytic metals include nickel; nickel and cobalt; nickel and copper; nickel and copper and magnesium; nickel and cobalt and magnesium. The most preferred metal is nickel. The support is characterized by processing a particular pore size distribution. A high percentage of pores when normalized on a maximum pore size of about 19.99 nm are in the range of up to 4.99 nm, the percentage of pores in this size range from about 30% or more, preferably about 35 to 100%, more preferably about 40 to 100%, pores of 5 to 19.99 nm constituting the balance, preferably the percentage of pores in the range of about 5 up to about 9.99 nm ranging from about 30% or less, preferably about 5 to 25%, more preferably about 10 to 25%, pores of 10 nm to 19.99 nm constituting the balance.

The support may comprise one or more ordered mesoporous materials with a unique structure and pore geometry as described below. Preferred ordered mesoporous materials are inorganic, porous, non-layered materials which, in their calcined forms exhibit an X-ray diffraction pattern with at least one peak at a d-spacing greater than about 18 Angstrom Units (Å). They also have a benzene adsorption capacity of greater than 15 grams of benzene per 100 grams of the material at 50 torr and 25° C. Preferred ordered mesoporous materials that may be used in the present invention, are those ordered mesoporous materials that may be synthesized using amphiphilic compounds as directing agents. Examples of such materials are described in U.S. Pat. No. 5,250,282, the whole contents of which are hereby incorporated by reference. Examples of amphiphilic compounds are also provided in Winsor, Chemical Reviews, 68(1), 1968. Other suitable ordered mesoporous materials of this type are also described in "Review of Ordered Mesoporous Materials", U. Ciesla and F. Schuth, Microporous and Mesoporous Materials, 27(1999), 13149. Such materials include but are not limited to materials designated as SBA (Santa Barbara) such as SBA-2, SBA-15 and SBA-16, materials designated as FSM (Folding Sheet Mechanism) such as FSM-16 and KSW-2, materials designated as MSU (Michigan State) such as MSU-S and MSU-X, materials designated as TMS or Transition Metal Sieves, materials designated as FMMS or functionalized monolayers on mesoporous supports and materials designated as APM or Acid Prepared Mesostructure. In a preferred form, the support material is characterized by a substantially uniform hexagonal honeycomb microstructure with uniform pores having a cell diameter greater than 2 nm and typically in the range of 2 to 50 nm, preferably 3 to 30 nm and most preferably from 3 to 20 nm. Particularly preferred ordered mesoporous materials are the silicate or aluminosilicate ordered mesoporous materials designated as M41S such as MCM-41, MCM-48 and MCM-50. These ordered mesoporous materials are described in detail in U.S. Pat. No. 5,102,643, the whole contents of which are hereby incorporated by reference. A particularly suitable sub-class of this family of materials for use in the present invention are the mesoporous silicas designated as MCM-41 and MCM-48. Most prominent among these materials is an ordered mesoporous material identified as MCM-41, which is usually synthesized as a metallosilicate with Broensted acid sites by incorporating a tetrahedrally coordinated trivalent element such as Al, Ga, B, or Fe within the silicate framework. The preferred forms of these materials are the aluminosilicates although other metallosilicates may also be utilized. MCM-41 is characterized by a microstructure with a uniform, hexagonal arrangement of pores with diameters of at least about 2 nm: after calcination it exhibits an X-ray diffraction pattern with at least one d-spacing greater than about 18 Å and a hexagonal electron diffraction pattern that can be indexed with a $d_{100}$ value of greater than about 18 Å, which corresponds to the d-spacing of the peak in the X-ray diffraction pattern. The MCM-41 molecular sieves generally have a $SiO_2/Al_2O_3$ molar ratio when alumina is present that is greater than 100, preferably greater than 200, and most preferably greater than 300. This material is described below and in detail in Ser. No. 07/625,245, now U.S. Pat. No. 5,098,684 (Kresge et al) and U.S. Pat. No. 5,102,643 to Kresge et al, both of which are incorporated by reference herein in their entirety.

The ordered mesoporous materials may be crystalline, that is having sufficient order to provide a diffraction pattern such as, for example, by X-ray, electron or neutron diffraction, following calcination, with at least one peak. These mesoporous materials may be characterized by their structure, which includes large pore windows as well as high sorption capacities.

Ordered mesoporous materials as used herein can be distinguished from other porous inorganic solids by the regularity of their large open pores, whose pore size more nearly resembles that of amorphous or paracrystalline materials, but whose regular arrangement and uniformity of size (pore size distribution within a single phase of, for example, +/−25%, usually +/−15% or less of the average pore size of that phase) resemble more those of crystalline framework materials such as zeolites. The term "hexagonal" is intended to encompass not only materials that exhibit mathematically perfect hexagonal symmetry within the limits of experimental measurement, but also those with significant observable deviations from that ideal state. A working definition as applied to the microstructure of the ordered mesoporous support material would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as +/−25% random deviation from the average repeat distance between adjacent channels still clearly give recognizable images of the present ordered mesoporous materials.

The ordered mesoporous materials as used for preparation of the catalyst support preferably have the following composition:

$$M_{n/q}(W_aX_bY_cZ_dO_h)$$

wherein W is a divalent element, such as a divalent first row transition metal, e.g., manganese, cobalt and iron, and/or magnesium, preferably cobalt; X is a trivalent element, such as aluminum, boron, iron and/or gallium, preferably aluminum; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar average valence of M; n/q is the number of moles or mole fraction of M; a, b, c, and d are mole fractions of W, X, Y and Z, respectively; h is a number of from 1 to 2.5; and (a+b+c+d)=1. A preferred embodiment of the above crystalline material is when (a+b+c) is greater than d, and h=2. A further embodiment is when a and d=0, and h=2. In the as-synthesized form, the mesoporous material has a composition, on an anhydrous basis, expressed empirically as follows:

$$rRM_{n/q}(W_aX_bY_cZ_dO_h)$$

wherein R is the total organic material not included in M as an ion, and r is the coefficient for R, i.e., the number of moles or mole fraction of R. The M and R components are associated with the material as a result of their presence during synthesis of the material and are easily removed or, in the case of M, replaced by post-synthesis methods hereinafter more particularly described.

To the extent desired, the original M, e.g., ammonium, sodium or chloride, ions of the as-synthesized material can be replaced in accordance with techniques well known in the art, at least in part, by ion exchange with other ions. Preferred replacing ions include metal ions, hydrogen ions, hydrogen precursor, e.g., ammonium, ions and mixtures thereof. Other ions include rare earth metals and metals of Groups IA (e.g., K), IIA (e.g., Ca), VIIA (e.g., Mn), VIIIA (e.g., Ni), IB (e.g., Cu), IIB (e.g., Zn), IIIB (e.g., In), IVB (e.g., Sn), and VIIB (e.g., F) of the Periodic Table of the Elements (Sargent-Welch Co. Cat. No. S-18806, 1979) and mixtures thereof.

The preferred ordered mesoporous materials for use in the process of the present invention are ordered mesoporous silicas. The most preferred ordered mesoporous silicas are those designated as M41S, with the most preferred being MCM-41.

Examples of mesoporous materials that may be used in the process of the present invention are the mesoporous silicas as described in and prepared according to U.S. Pat. No. 5,951,962, the disclosure of which is incorporated herein in its entirety. In that embodiment, mesoporous silica is prepared by converting a silica precursor in a water and polymer dispersion containing reaction medium. The preferred polymer dispersion is a cationic polymer.

High surface area mesoporous alumina solids may also be used in preparing the catalyst supports for use in the processes of the present invention; such high surface area mesoporous alumina solids may be prepared according to the methods described in U.S. Pat. No. 6,238,701, the disclosure of which is incorporated herein in its entirety.

The support may also consist of conventional amorphous and/or crystalline macroporous materials. Materials of mixed porosity which contain both macropores and mesopores, such as those described in U.S. Pat. Nos. 5,936,126, 6,248,924 and 6,284,917 the disclosures of which are incorporated herein by reference in their entirety can also be used as supports. These materials can be used as supports by themselves or in combination with each other or with the mesoporous and/or ordered mesoporous materials previously described in preparing catalysts useful in the present process.

Conventional amorphous and/or crystalline macroporous materials suitable as binders have a mean pore diameter of at least about 50 nm, preferably at least about 100 nm, in particular at least about 500 nm. Preferably these macroporous materials have a BET surface area that is at most about 30 $m^2/g$, preferably at most about 15 $m^2/g$, more preferably at most about 10 $m^2/g$ in particular at most about 5 $m^2/g$ and more preferably at most about 3 $m^2/g$. The mean pore diameter of theses macroporous materials is preferably from about 100 nm to about 20000 nm, and more preferably from about 500 nm to about 5000 nm, and most preferably 500 nm to 1000 nm. The surface area of these macroporous materials is preferably from about 0.2 to about 15 $m^2/g$, more preferably from about 0.5 to about 10 $m^2/g$, in particular from about 0.5 to about 5 $m^2/g$ and more preferably from about 0.5 to about 3 $m^2/g$. Such macroporous material can be used in admixture with the mesoporous support material.

The surface area of the conventional amorphous and/or crystalline macroporous materials and mixed porosity materials may be determined by the BET method using $N_2$ adsorption, in particular in accordance with DIN 66131. The mean pore diameter and the size distribution may be determined by $N_2$ porosimetry. The BJH adsorption isotherms were measured using ASTM method D-4222 "Standard test method for determination of nitrogen adsorption and desorption isotherms of catalysts by static volumetric measurements".

The conventional amorphous and/or crystalline macroporous materials and mixed porosity materials, for example, macropore containing activated carbon, silicon carbide, aluminum oxide, silicon dioxide, titanium dioxide, zirconium dioxide, magnesium oxide, zinc oxide or mixtures of two or more thereof, with preference being given to using macropore containing alumina.

When a mesoporous and/or ordered mesoporous material is used in combination with macroporous material and/or mixed porosity matrix material, the finished catalyst may be a composition comprising a support matrix of from 90 to 10% by weight mesoporous material and 10 to 90% by weight macroporous material, preferably 80 to 20% by weight mesoporous material and 20 to 80% by weight macroporous material, more preferably 80 to 40% by weight mesoporous and 20 to 60% by weight of macroporous material. A particularly preferred composition comprises a support matrix of 70 to 60%, ideally 65% by weight mesoporous material and 30 to 40%, ideally 35% by weight macroporous material.

In the present invention the final catalyst may consist solely of one or more active metals deposited on the surfaces of one or more of the previously described support materials. The catalyst can be free of added inorganic binder but the use of the catalyst in the bound form is also encompassed. The supports with or without active metal deposited thereon may be shaped into a wide variety of particle sizes. Generally, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, they can be extruded before drying or partially dried and then extruded. In these embodiments various extrusion or forming aids may be used in the extrusion or forming process along with one or more solvents, all techniques which are well known in the art.

The support material with or without one or more catalytic metals deposited thereon may be formed into composites with inorganic binder or matrix materials that are resistant to the temperatures and other conditions employed in the present processes. Such binder or matrix materials may also aid in the formation and manufacture of the final catalyst. Such binders or matrix materials include active and inactive materials and synthetic or naturally occurring zeolites as well as inorganic materials such as clays and/or oxides such as alumina, silica or silica-alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. These materials may be incorporated into naturally occurring clays, e.g., bentonite and kaolin, to improve the crush strength of the catalyst under commercial operating conditions and function as binders or matrices for the catalyst. The support containing one or more catalytically active metals may be formed into a composition comprising the macroporous matrix material in amounts from 99:01 to 05:95 by weight, preferably from 99:01 to 10:90, more preferably from 99:01 to 20:80, and most preferably from 99:01 to 50:50, catalyst support to matrix material. Preferably, if used, the additional matrix material is kept to a minimum typically less than 50 wt % of the combined weight of catalyst support and matrix material, ideally less than 40 wt %, preferably less than 30 wt %, more preferably less than 20 wt %, more preferably less than 15 wt %, most preferably less than 10 wt % and in a most preferred embodiment less than 5 wt %. Formation of the composition may be achieved by conventional means including mulling the materials together followed by extrusion of pelletizing into the desired finished catalyst particles. Ideally the additional binder matrix material is selected from the previously described conventional amorphous and/or crystalline macroporous material or is a material of mixed porosity, i.e., both macroporous and mesoporous. Another catalyst meeting the requirement recited herein for pore size distribution is a commercially available nickel loaded catalyst, Ni 5249-P, from Engelhard Corporation.

The metal loaded catalyst useful in the present process, in addition to exhibiting the pore size distribution previously recited is also characterized by having a total BET surface area above about 50 $m^2/g$, preferably about 200 to 1000 $m^2/g$, more preferably about 250 to 900 $m^2/g$, and a micropore volume of above 0.05 $cm^3/g$, preferably above 0.10 $cm^3/g$, more preferably above 0.20 $cm^3/g$. It has been found that in the process for the production of severely sterically hindered amino ether alcohols, bis amine polyalkenyl ether, and mixtures thereof, from amine and glycol, catalysts having the pore size distribution recited herein exhibit selectivity equivalent to or superior to that exhibited by prior art catalysts, which do not possess the current pore size distribution, and at equivalent or superior glycol conversion levels, but at lower metal loadings. Thus, on a unit metal basis, the catalysts described herein possessing pore size distribution in the recited ranges are more active and more selective than catalyst containing a much higher loading of active metal. Conversely, when a catalyst possessing the recited pore size distribution is loaded with the same amount of metal as the prior art catalyst, the process exhibits a selectivity to desired product and a level of glycol conversion which are considerably higher than that achieved in the prior art processes.

The catalytic metal component can be deposited on the support using any known technique. Thus, impregnation by the incipient wetness technique can be used, as well as spraying, dipping, immersion, soaking, etc., including multiple immersion, spraying, soaking, or dipping or any combination of such techniques with intermediate drying or even activation between each application of catalytic metal. The particular method or sequence of steps is left to the practitioner skilled in the typical catalyst preparation methods. The catalytic metal is typically applied in the form of an aqueous solution of one or more metal salts. Suitable catalytic metal salts are the nitrites, nitrosyl nitrate, halides, carbonates, carboylates, acetylacetonates, chloro complexes, nitrite complexes, preferably nitrates and nitrosyl nitrates. Preferably the catalytic metal salt is a nickel salt.

In co-pending application U.S. Ser. No. 60/545,197 filed Feb. 17, 2004, it is disclosed that a preferred technique for the deposition of catalytic metal on the support involves the use of an organic dispersion aid. Suitable organic compounds which can be employed are those that contain one or more amino groups, such as amines, amino acids, or hydroxy alkyl amines. Such molecules are employed for their ability to form organic complexes with the metal salts, preferably nickel salt, used. The metal salt, the organic dispersion aid or a performed complex of metal salt and organic dispersion aid, made by mixing the metal salt and organic dispersion aid, in any sequence or simultaneously in the case of the use of a separate metal salt and organic dispersion aid can be exchanged on to the support by any of the previously described and known techniques by impregnation on physical admixture, including steeping, i.e. soaking or incipient wetness, the support in the appropriate solution or series of solutions or by dipping, spraying or any other suitably technique, again using the appropriate solution or series of solutions.

The support, once loaded, can be handled as is appropriate for metal loaded catalysts. The metal loaded catalyst is dried. In the case of the organic complex loaded catalyst the organic complex can be either partially or fully decomposed, then calcined or pyrolyzed, activated in a reducing atmosphere such as hydrogen and/or CO to reduce the metal to catalytically active elemental metal, passivated if not being used immediately and reactivated in a reducing atmosphere before use.

In general, and regardless of the technique used to load the metal salt onto the support, catalyst activation/reduction is at any temperature and for a time sufficient to reduce the metal salt to reduced metal. The catalyst comprises about 2.5 to about 80 wt % reduced metal, preferably about 10 to about 65 wt % reduced metal based on the whole reduced catalyst.

The higher the degree of activation/reduction the more active the catalyst. It is preferred that the metal loaded catalyst be activated in a reducing atmosphere at temperatures in the range of about 200 to 500° C., preferably 200 to 400° C. for from about 2 to 24 hours, preferably about 2 to 16 hours. In the case of nickel, for example, it is preferred that the reduction temperature be high enough to convert the metal oxide or salt used into at least about 10% reduced metal, preferably at least about 12% reduced metal, more preferably at least about 14% reduced metal. An initial reduction at temperatures of about 350° C. to 50020 C., preferably about 400° C. for at least 1 hour is desirable for nickel.

It has been found that activation/reduction at about 400° C. for about 1 to 2 hours produces a catalyst for use in the present process which exhibits an enhanced initial level of activity and selectivity for the production of EETB from the amine/glycol mixture, but that this enhancement diminishes over time at the higher levels of glycol conversion. However, the enhanced performance initially exhibited can be advantageously captured by running the reaction for shorter periods of time and to lower levels of glycol conversion, followed by reactivation at about 400° C. for 1 to 2 hours between each use.

In the examples, except where otherwise indicated, the data presented in the tables were obtained by using the normalized weight percent values of all products and all reactants from the GC. The conversion was calculated by the following method: the concentration of DEG as charged minus the DEG concentration at the time point of interest, this quantity divided by the DEG concentration as charged and multiplied by 100 to give a percent DEG converted. Note that one mole of DEG reacts with one mole of TBA to form one mole of EETB, and normalizing on the basis of DEG conversion takes this into consideration. In some of the examples the % DEG converted is reported as negative. This occurs for the low activity catalysts, and is an artifact of the normalization of the sample and the volatilization of the TBA (bp 44° C.) upon sampling at high temperature. The GC reports the relative concentration of each reactant and product component in the entire sample. Because small amounts of TBA are evaporated, the relative amount of DEG in the sample is reported to be higher. When compared with the initial concentration at the reactor loading, the DEG appears to have increased in concentration. The conversion values were reported as calculated, and although they are reported as negative, they should effectively be considered zero conversion. This tendency would also occur to some extent in the other calculations of conversion, thus these numbers are likely represent a lower bound on conversion, but should occur to the same degree in all the samples and a meaningful comparison between runs can be made. The weight percent ratios for the EETB/TBM and EETB/Bis-SE ratios were obtained by simply taking the ratio of the respective weight percents from the GC trace. The molar ratios were determined by converting the ratio from grams/grams to moles/moles by dividing the weight percent of each component by its molecular weight.

EXAMPLES

A series of experiments was run to evaluate the performance and utility of various catalysts for the production of EETB from mixtures of tertiary-butyl amine (TBA) and diethylene glycol (DEG) and to compare against the current art.

In some of the examples, catalyst samples were charged into the autoclave as received and used without hydrogen re-activation. In those cases, the reduced Ni content in the catalyst was estimated by TGA measurement of the reduced metal content in the catalyst after one-hour reduction in hydrogen at 200° C. or at 180° C., as indicated in each instance. This is believed to be a close approximation of the degree of reduction taking place in the autoclave after it is charged, pressurized with hydrogen and brought to the reaction temperature.

Example 1(a)

A mixture of TBA/DEG (2:1 mole ratio) was reacted over a commercial catalyst secured from a vendor and meeting the recited requirements. 1.56 g of the nickel loaded catalyst which had been used in a different run was reused in this example. It was not subjected to a pre-reuse reactivation step. The techniques and condition used by the catalyst manufacturer for its initial activation are not known. The catalyst reportedly contains 64% nickel with a degree of reduction of 0.35. 100.5 g of TBA and 73.0 g of DEG (2:1 mole ratio TBA/DEG) was employed. Starting hydrogen pressure at room temperature was 100 psig. The TBA and DEG were loaded into the autoclave at room temperature under nitrogen. The contents of the autoclave were heated at 180° C. with stirring at 1800 rpm for 7 hours with GC sampling at one hour intervals. Based upon reduction experiments performed on a different batch of this catalyst at 180° C. for 1 hour in hydrogen, it is believed the reduced metal content of this commercial catalyst is about 42% based on the whole reduced catalyst, the reduction occurring in-situ during the process step. Total reactor pressure at 180° C. was 372 psig. The results are presented below:

describes how many moles of EETB are produced per mole TBM at a given level of DEG conversion. The higher the EETB/TBM mole ratio at a given level of DEG conversion, the more selective the catalyst. The catalysts which exhibit high EETB/TBM mole ratios at high levels of DEG conversion are preferred.

Example 1(b)

A mixture of TBA/DEG (2:1 mole ratio) was reacted over a commercial nickel loaded catalyst secured from a vendor and meeting the recited requirement. 1.62 g of fresh catalyst, the same as in Example 1(a) but a fresh, unused sample, was employed as received from the supplier. The techniques and conditions used by the catalyst manufacturer for its initial activation are not known. The catalyst reportedly contains 64% nickel with a degree of reduction of 0.35. 109.3 g of TBA and 79.3 g of DEG were loaded into an autoclave at room temperature under nitrogen. Starting hydrogen pressure at room temperature was 100 psig. The contents of the autoclave were heated at 180° C. with stirring at 1800 rpm for 7.5 hours with GC sampling at the intervals indicated in the table below. Based upon reduction experiments performed in a sample of the catalyst from a different batch at 180° C. for 1 hour in Recycled Catalyst at 180° C. (100 psig of $H_2$, 2:1 TBA/DEG), Unactivated

| Fraction # | Time (hrs) | DEG Conv (%) | EETB/TBM (wt) | EETB/TBM (molar) | EETB/Bis SE (wt) | EETB/Bis SE (molar) |
|---|---|---|---|---|---|---|
| 16-1 | 1 | −10.5 | 37.3 | 33 | 137.2 | 184.1 |
| 16-2 | 2 | −1.5 | 54.0 | 48 | 185.4 | 248.7 |
| 16-3 | 3 | 3.4 | 38.5 | 34 | 121.1 | 162.4 |
| 16-4 | 4 | 14.2 | 28.7 | 25 | 86.8 | 116.4 |
| 16-5 | 6 | 43.5 | 14.1 | 13 | 43.8 | 58.8 |
| 16-6 | 7 | 44.4 | 12.3 | 11 | 41.4 | 55.6 |

TBM is N-tertiary-butylmorpholine, an undesirable by-product.
Bis-SE is 2,2'-tertiary-butylamino ethyl ether (or bis(tertiary-butylaminoethoxy) ethane).

After 7 hours at 180° C., the mole ratio of EETB/TBM (TBM is N-tertiary-butyl morpholine, an undesirable by-product) was 11 at a DEG conversion level of 44.4%. The mole ratio of EETB/TBM is a convention used to compare selectivity of the catalyst being evaluated. It essentially hydrogen, it is believed the reduced metal content of this commercial catalyst is about 42% based on the whole reduced catalyst, the reduction occurring in-situ during the process step. Total reactor pressure at 180° C. was 267 psig. The results are presented below:

180° C. no activation (100 psig of $H_2$, 2:1 TBA:DEG)

| Fraction # | Time (hrs) | Pressure (psi) | DEG Conv (%) | EETB/TBM (wt) | EETB/TBM (molar) | EETB/Bis SE (wt) | EETB/Bis SE (molar) |
|---|---|---|---|---|---|---|---|
| 59-1 | 1 | 267 | 11.4 | 153.1 | 136 | 1.5 | 2.0 |
| 59-2 | 2 | 262 | 24.0 | 86.0 | 76 | 1.8 | 2.4 |
| 59-3 | 3 | 262 | 20.5 | 57.8 | 51 | 0.8 | 1.0 |
| 59-4 | 4 | 262 | 35.3 | 32.4 | 29 | 0.6 | 0.8 |
| 59-5 | 7.5 | 263 | 60.8 | 10.9 | 10 | 0.4 | 0.6 |

Example 2

110.8 g of TBA and 78.4 g of DEG (2:1 mole ratio) were added to an autoclave under nitrogen at room temperature. 1.6 g of fresh nickel loaded catalyst of Example 1(b) (used as received from the supplier) was employed in the autoclave. Starting hydrogen pressure at room temperature was 100 psig. Heating was to 200° C. with stirring at 1800 rpm for 6 hours with GC sampling every hour. Total reactor pressure at 200° C. was 355 psig. Based upon reduction experiments done on two different batches of this catalyst at 200° C. for 1 hour in hydrogen, it is believed the reduced metal content is about 40 to 43% based on the whole reduced catalyst, in this case the reduction occurring in-situ during the process step. The results are presented below:

| Fraction # | Time (hours) | DEG Conv (%) | EETB/TBM (wt) | EETB/TBM (molar) | EETB/Bis SE (wt.) | EETB/Bis SE (molar) |
|---|---|---|---|---|---|---|
| 30-1 | 1 | 21.0 | 79.0 | 70 | 135.7 | 182.1 |
| 30-2 | 2 | 57.0 | 21.8 | 19 | 46.2 | 62.0 |
| 30-3 | 3 | 68.7 | 12.4 | 11 | 22.8 | 30.5 |
| 30-4 | 4 | 78.8 | 7.8 | 7 | 14.0 | 18.8 |
| 30-5 | 5 | 87.0 | 4.8 | 4 | 9.6 | 12.9 |
| 30-6 | 6 | 91.1 | 3.7 | 3 | 7.2 | 9.7 |

200° C. (100 psig of $H_2$, 2:1 TBA/DEG), Unactivated

After 6 hours DEG conversion was 91.1% with an EETB/TBM molar ratio of 3.

Comparing Example 2 with Examples 1(a) and (b) it is clear that operation at higher temperature produces more product sooner. In Example 2, an EETB/TBM molar ratio of 11 is achieved at a DEG conversion level of 68.7% (after 3 hours) whereas in Example 1(a) an EETB/TBM molar ratio of 11 was achieved at a DEG conversion level of 44.4% (after 7 hours), while in Example 1(b) an EETB/TBM at a ratio of 10 was achieved at a DEG conversion level of 60.8% after 7.5 hours.

Example 3

106.2 g of TBA and 74.4 g of DEG (2:1 molar ratio) were loaded into an autoclave under nitrogen at room temperature. 1.59 g of fresh nickel loaded catalyst of Example 1(b) was used, but was activated prior to use at 200° C. in hydrogen (1 psi of hydrogen flow at 50 cc/min for 19 hours) resulting in about 46% reduced nickel metal based on the whole reduced catalyst. Starting hydrogen pressure at room temperature was 100 psig. Heating was to 180° C. for 6 hours with GC sampling at the 1st and 6th hours. Total reactor pressure at 180° C. with stirring at 1800 rpm was 372 psig. The results are presented below:

| Fraction # | Time (hrs) | DEG Conv (%) | EETB/TBM (wt) | EETB/TBM (molar) | EETB/Bis SE (wt) | EETB/Bis SE (molar) |
|---|---|---|---|---|---|---|
| 20-1 | 1 | 21.1 | 46.3 | 41 | 111.6 | 149.7 |
| 20-2 | 6 | 74.6 | 6.3 | 6 | 13.3 | 17.8 |

180° C. (100 psig, $H_2$, 2:1 TBA/DEG), Activated at 200° C. in $H_2$

After 6 hours the EETB/TBM molar ratio was 6 at a DEG conversion level of 74.6%.

Example 4(a)

109.1 g of TBA and 79.2 g of DEG (2:1 molar ratio) were loaded into an autoclave under nitrogen at room temperature. 1.61 g of fresh nickel loaded catalyst of Example 1(b) was used, but was activated prior to use at 200° C. in hydrogen (1 psi of hydrogen flow at 50 cc/min for 17 hours) resulting in about 46% reduced nickel metal based on the whole reduced catalyst. Starting hydrogen pressure at room temperature was 100 psig. Heating was to 200° C. with stirring at 1800 rpm for 4 hours with GC sampling every hour. Total reactor pressure at 200° C. was 374 psig. The results are presented below:

| Fraction # | Time (hrs) | Press (psi) | DEG Conv (%) | EETB/TBM (wt) | EETB/TBM (molar) | EETB/Bis SE (wt) | EETB/Bis SE (molar) |
|---|---|---|---|---|---|---|---|
| | | | | | 200 C.° (100 psig of $H_2$, 2:1 TBA:DEG) 200 C.° activation in $H_2$ (17 hours) | | |
| 58-1 | 1 | 369 | 36.3 | 28.5 | 25 | 0.9 | 1.2 |
| 58-2 | 2 | 383 | 58.5 | 13.6 | 12 | 0.7 | 0.9 |
| 58-3 | 3 | 389 | 74.9 | 8.0 | 7 | 0.5 | 0.7 |
| 58-4 | 4 | 389 | 85.2 | 4.6 | 4 | 0.5 | 0.7 |

0.1% oxygen in nitrogen for 30 minutes, followed by 0.3% oxygen in nitrogen for 30 minutes, followed by 10% oxygen in nitrogen for 30 minutes, and finally followed by 20% oxygen in nitrogen for 30 minutes. Before use, the passivated catalyst was subjected to a reactivation at 200° C. in 1 psi of hydrogen flow 50 cc/min for 18 hours resulting in a metallic reduced nickel content of about 53% based on the whole reduced catalyst. 104.8 g of TBA and 76.1 g of DEG (2:1 molar ratio charge) were added to the autoclave. Initial hydrogen pressure at room temperature was 100 psig. The reactor was heated to 200° C. for 4 hours and GC samples were taken every hour. Total reactor pressure at 200° C. with stirring at 1800 rpm was 386 psig. The results are presented below:

| Fraction # | Time (hrs) | DEG Conv (%) | EETB/TBM (wt) | EETB/TBM (molar) | EETB/Bis SE (wt) | EETB/Bis SE (molar) |
|---|---|---|---|---|---|---|
| | | Reduced at 400° C. in $H_2$ (200° C., 2:1 TBA/DEG, 100 psig of $H_2$) | | | | |
| 45-1 | 1 | 42.2 | 30.0 | 27 | | |
| 45-2 | 2 | 66.9 | 12.1 | 11 | 0.8 | 1.0 |
| 45-3 | 3 | 78.0 | 7.4 | 7 | 0.7 | 0.9 |
| 45-4 | 4 | 85.1 | 5.2 | 5 | 0.6 | 0.8 |

Example 4(b)

A 1.54 g sample of fresh nickel loaded catalyst of Example 1(b) was activated at 400° C. followed by catalyst passivation according to the following protocol was used: five gram sample of catalyst was activated by reduction at 400° C. in flowing hydrogen (200 cc/min $H_2$ and 50 cc/min $N_2$) for 1 hour at atmospheric pressure, the catalyst being heated at 2° C./min from room temperature to 400° C. and held at 400° C. for 1 hour. The so reduced catalyst was passivated to permit aerobic transfer to the autoclave for testing. Passivation was accomplished by cooling the reduced catalyst to room temperature under hydrogen flow. When cooled, the hydrogen was replaced by nitrogen and the catalyst was purged in nitrogen for an hour and gradually exposed to increasing concentrations of oxygen in nitrogen diluent. First, 0.02% oxygen in nitrogen was used for 30 minutes, followed by It is seen that at 2 hours, the DEG conversion level was 66.9% for an EETB/TBM molar ratio of 11.

This is to be compared with the results of Example 2 wherein a DEG conversion level of 68.7% for an EETB:TBM molar ratio of 11 was achieved only after 3 hours and with the result of Example 4(a) wherein a DEG conversion level of only 58.5% for a EETB:TBM molar ratio of 12 was achieved at 2 hours. This is indicative that the catalyst activated at high temperature is more active than the same catalyst used on an as received basis or one activated at only 200° C. before use.

Example 5

The Effect of Hydrogen Pressure was Investigated a) 1.62 g of fresh nickel loaded catalyst of Example 1(b) used as received from the supplier was employed to react 110.1 g of TBA with 77.8 g of DEG (2: molar ratio) charged to an autoclave at room temperature under nitrogen. Hydrogen starting pressure at room temperature was 50 psig. The reactor contents were heated at 180° C. with stirring at 1800 rpm for 7 hours with GC sampling every hour. Based upon reduction experiments performed on a sample of this catalyst from a different batch at 180° C. for 1 hour in hydrogen, it is believed the reduced metal content of this commercial catalyst is about 42% based on the whole reduced catalyst, the reduction occurring in-situ during the process step. Total reactor pressure at reaction temperature was 260 psig. The results are presented below:

| | | | Initial pressure 50 psig of H$_2$, (180° C. 2:1 TBA/DEG), not reactivated | | | |
|---|---|---|---|---|---|---|
| Fraction # | Time (hrs) | DEG Conv (%) | EETB/TBM (wt) | EETB/TBM (molar) | EETB/Bis SE (wt) | EETB/Bis SE (molar) |
| 37-1 | 1 | 4.0 | 179.6 | 160 | 301.1 | 403.9 |
| 37-2 | 2 | 22.2 | 97.6 | 87 | 143.7 | 192.8 |
| 37-3 | 3 | 26.2 | 46.6 | 41 | 67.9 | 91.1 |
| 37-4 | 4 | 30.2 | 31.4 | 28 | 42.8 | 57.4 |
| 37-5 | 5 | 45.4 | 20.6 | 18 | 30.4 | 40.8 |
| 37-6 | 6 | 60.4 | 12.8 | 11 | 22.0 | 29.5 |
| 37-7 | 7 | 59.2 | 13.6 | 12 | 16.8 | 22.6 | b) 106.2 g of TBA and 74.4 g of DEB (2:1 mole ratio) was charged to an autoclave reactor under nitrogen at room temperature. 1.59 g of fresh nickel loaded catalyst of Example 1(b) activated at 200° C. in 1 psi of hydrogen flow at 50 cc/min for 19 hours was employed leaving about 46% reduced nickel metal based on the whole reduced catalyst. Starting hydrogen pressure at room temperature was 100 psig. The reactor contents were heated at 180° C. with stirring at 1800 rpm for 6 hours. Total reactor pressure at 180° C. was 372 psig. The results are presented below.

| | | | 180° C. (100 psig of H$_2$, 2:1 TBA/DEG) | | | |
|---|---|---|---|---|---|---|
| Fraction # | Time (hrs) | DEG Conv % | EETB/TBM (wt) | EETB/TBM (molar) | EETB/Bis SE (wt) | EETB/Bis SE (molar) |
| 20-1 | 1 | 21.1 | 46.3 | 41 | 111.6 | 149.7 |
| 20-2 | 6 | 74.6 | 6.3 | 6 | 13.3 | 17.8 | c) 106.8 g of TBA and 75.5 g of DEG (2:1 molar ratio) were charged to an autoclave at room temperature under nitrogen. 1.57 g of fresh nickel loaded catalyst of Example 1(b) used as received, was added to the reactor. Starting hydrogen pressure was 300 psig. The contents were heated at 180° C. with stirring at 1800 rpm for 8 hours with GC sampling at the times indicated below. As previously stated above, it is believed the reduced metal content of this catalyst is about 42% based on the whole reduced catalyst, the reduction occurring in-situ during the process step conducted at 180° C. in hydrogen. Total reactor pressure at 180° C. was 501 psig. The results are presented below:

| | | | Initial pressure 300 psig of H$_2$, (180° C. 2:1 TBA/DEG), not reactivated | | | |
|---|---|---|---|---|---|---|
| Fraction # | Time (hrs) | DEG Conv (%) | EETB/TBM (wt) | EETB/TBM (molar) | EETB/Bis SE (wt) | EETB/Bis SE (molar) |
| 35-1 | 1 | 0.0 | | | | |
| 35-2 | 2 | −6.8 | 46.7 | 41 | 310.8 | 417.0 |
| 35-3 | 3 | 4.2 | 31.3 | 28 | 188.7 | 253.2 |
| 35-4 | 5 | 11.5 | 20.2 | 18 | 120.5 | 161.7 |
| 35-5 | 6 | 26.2 | 15.6 | 14 | 98.1 | 131.7 |
| 35-6 | 8 | 36.0 | 11.3 | 10 | 59.3 | 79.5 |

From the data for Example 5(a) (b) and (c) plotted on FIG. 1 it is seen that operation at 50 and 100 psig initial hydrogen pressure gave results that are fairly equivalent, with the reaction at 50 psig being initially favored at lower DEG conversion levels (DEG conversion level of about 20 to 30%). High initial hydrogen pressure (300 psig) is not beneficial for the reaction because it inhibits the initial dehydrogenation step.

Example 6

The Affect of Changing the TBA:DEG Molar Ratio was Investigated.

(a) 75.5 g of TBA and 109.6 g of DEG 1:1 molar ratio) was charged to an autoclave under nitrogen at room temperature. 1.59 g of fresh nickel loaded catalyst of Example 1(b) was used as received form the supplier. Starting hydrogen pressure at room temperature was 100 psig. Reactor contents were stirred at 1800 RPM and heated at 180° C. for 7 hours with GC sampling every hour. As previously stated above, it is believed the reduced metal content of this catalyst is about 42% based on the whole reduced catalyst, the reduction occurring in-situ during the process step conducted at 180° C. in hydrogen. Total reactor pressure at 180° C. was 235 psig. The results are presented below:

| Run # | Temperature (° C.) | Time (hours) | TBA:DEG (wt) | DEG Conv (%) | EETB/TBM (molar) |
|---|---|---|---|---|---|
| 27 | 180 | 6 | 3:1 | 72 | 13 |

Figure 2:
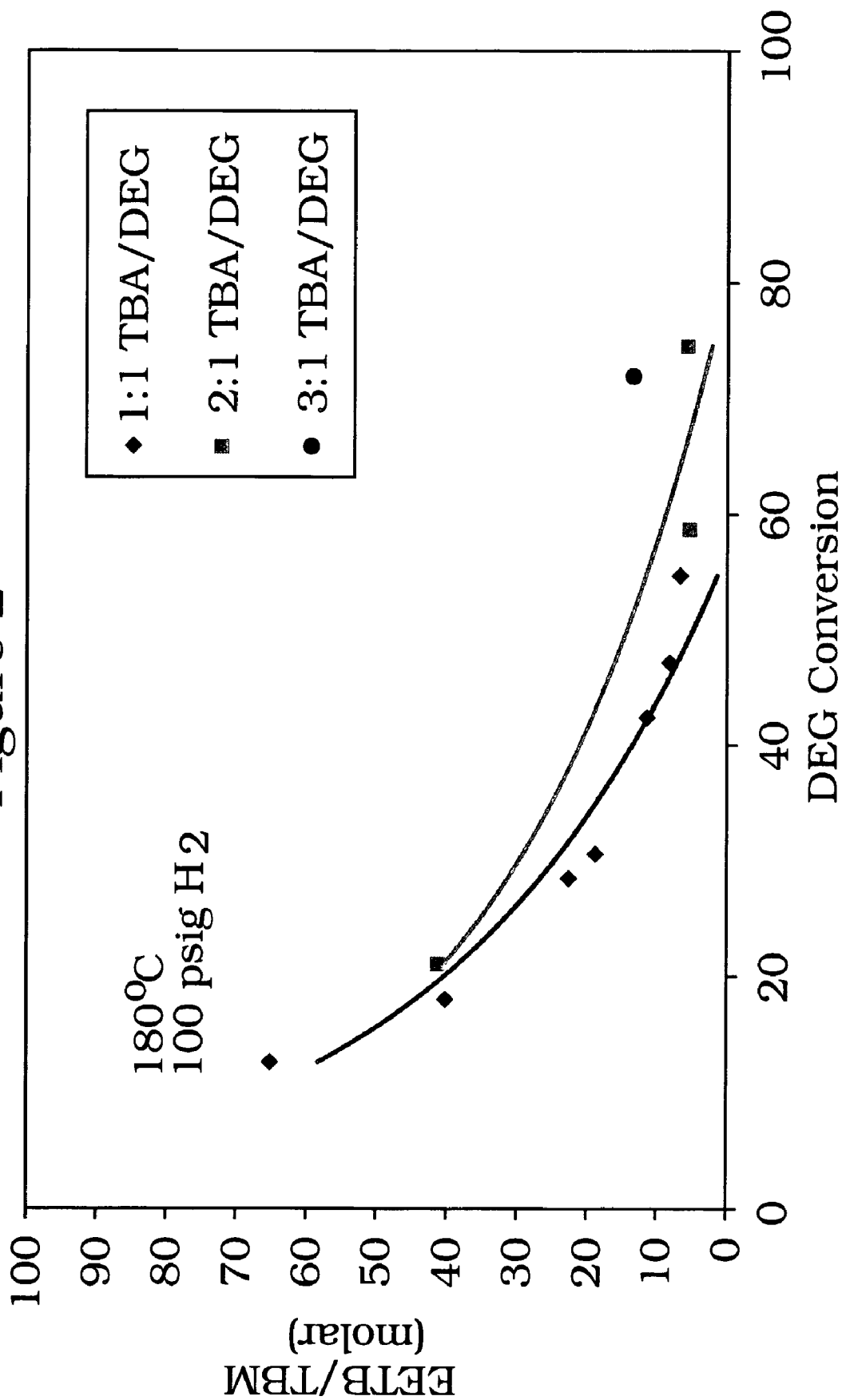
FIG. 2 is a plot of the level of DEG conversion versus EETB/TBM ratio for three runs, one run employing a 1:1 TBA/DEG ratio, the second a 2:1 TBA/DEG ratio, and the third a 3:1 TBA/DEG ratio.

The results are summarized in FIG. 2 which shows that operation at the higher TBA/DEG ratio results in higher EETB/TBM ratios at equivalent levels of DEG conversion. A small improvement in the EETB/TBM ratio can be observed for the synthesis conducted at the 3:1 TBA:DEG ratio, even at slightly higher DEG conversion. Directionally higher TBA/DEG ratios show an improved selectivity to the desired EETB product.

| | | 1:1 TBA:DEG (100 psig of $H_2$, 180° C.), not reactivated | | | |
|---|---|---|---|---|---|
| Fraction # | Time (hrs) | DEG Conv (%) | EETB/TBM (wt) | EETB/TBM (molar) | EETB/Bis SE (wt) | EETB/Bis SE (molar) |
| 39-2 | 1 | 12.6 | 73.4 | 65 | | |
| 39-3 | 2 | 18.0 | 45.3 | 40 | 151.5 | 203.3 |
| 39-4 | 3 | 28.4 | 25.5 | 23 | 87.1 | 116.9 |
| 39-5 | 4 | 30.6 | 21.2 | 19 | 66.7 | 89.5 |
| 39-6 | 5 | 42.4 | 12.8 | 11 | 51.4 | 69.0 |
| 39-7 | 6 | 47.1 | 9.3 | 8 | 44.2 | 59.3 |
| 39-8 | 7 | 54.7 | 7.6 | 7 | 33.8 | 45.4 |

(b) 106.2 g of TBA and 74.4 g of DEB (2:1 mole ratio) was charged to an autoclave reactor under nitrogen at room temperature. 1.59 g of fresh nickel loaded catalyst of Example 1(b) activated at 200° C. in 1 psi of hydrogen flow at 50 cc/min for 19 hours was employed having about 46% reduced nickel metal based on the whole reduced catalyst. Starting hydrogen pressure at room temperature was 100 psig. The reactor contents were heated at 180° C. with stirring at 1800 rpm for 6 hours. Total reactor pressure at 180° C. was 372 psig. The results are presented below:

| | | 180° C. (100 psig of $H_2$, 2:1 TBA/DEG) | | | |
|---|---|---|---|---|---|
| Fraction # | Time (hrs) | DEG Conv (%) | EETB/TBM (wt) | EETB/TBM (molar) | EETB/Bis SE (wt) | EETB/Bis SE (molar) |
| 20-1 | 1 | 21.1 | 46.3 | 41 | 111.6 | 149.7 |
| 20-2 | 6 | 74.6 | 6.3 | 6 | 13.3 | 17.8 |

(c) 198.0 g of TBA and 95.8 g of DEG (3:1 mole ratio) were charged to the reactor under nitrogen at room temperature. 2.28 g of fresh nickel loaded catalyst of Example 1(b) was charged to the reactor as received from the supplier. Initial hydrogen pressure at room temperature as 100 psig. Contents of the reactor were heated at 180° C. with stirring at 1800 rpm for 6 hours. As previously stated above, it is believed the reduced metal content of this catalyst is about 42% based on the whole reduced catalyst, the reduction occurring in-situ during the process step conducted at 180° C. in hydrogen. The final reactor product was analyzed by NMR. The results are presented below.

Example 7

The procedure of co-pending application U.S. Ser. No. 60/545,197 filed Feb. 17, 2004, was employed to make a nickel on ordered mesoporous support catalyst. 15.0 g of alumina bound MCM-41 extrudate support (whereby MCM-41 is ordered silicous mesoporous material and alumina is the matrix) was impregnated to the incipient wetness point with a solution prepared by dissolving 19.28 g of nickel nitrate hexahydrate in 6.82 g of water and 2.47 g of triethanolamine. The sample was then dried in air at 100° C. for four hours. The dried sample was calcined in flowing air by gradually ramping the temperature according to the following protocol to temper the vigorous oxidation reaction between nickel nitrate and the aminoalcohol: 2° C./minute to 140° C. and hold for 30 minutes, 1° C./minute to 175° C. and hold for 30 minutes. Five gram sample of the catalyst was activated by reduction at 400° C. in flowing hydrogen (200 cc/min $H_2$ and 50 cc/min $N_2$) for 1 hour at atmospheric pressure by heating the catalyst at 2°/min from room temperature up to 400° C. for 1 hour. The so reduced catalyst was passivated to permit aerobic transfer to the autoclave for testing. Passivation was accomplished by cooling the reduced catalyst to room temperature under hydrogen flow. When cooled, the hydrogen was replaced by nitrogen and the catalyst was purged in nitrogen for an hour and gradually exposed to increasing concentrations of oxygen in nitrogen diluent. First, 0.02% oxygen in nitrogen was used for 30 minutes, followed by 0.1% oxygen in nitrogen for 30 minutes, followed by 0.3% oxygen in nitrogen for 30 minutes, followed by 10% oxygen in nitrogen for 30 minutes, and finally followed by 20% oxygen in nitrogen for 30 minutes.

Example 8

The catalyst of Example 7 was employed in the example. 1.59 g of Ni (19.5%) on alumina bound MCM-41 (crushed into a powder) was employed to synthesize EETB. Prior to use, the catalyst was re-activated at 200° C./1 psi of hydrogen at 50 cc/min for 18 hours in-situ. The catalyst had a reduced nickel metal content of 14% based on the total weight of the reduced catalyst. 108.0 g of tertiary-butyl amine and 76.4 g of diethylene glycol, a 2:1 mole ratio of TBA:DEG, were then charged to the reactor under nitrogen at room temperature. The contents of the autoclave reactor were heated at 180° C. with stirring at 1800 rpm for 6 hours with GC sampling hourly intervals. Reactor temperature was held at 180° C. Initial hydrogen pressure at room temperature was 100 psig, total reactor pressure at 180° C. was 280 psig. The results are presented below:

Results of Example 8.

| Time (h) | Products (GC Weight %) | | | | EETB/TBM mole ratio | EETB/Bis-SE mole ratio | % Conversion Based on DEG |
|---|---|---|---|---|---|---|---|
| | Bis-SE | EETB | TBM | DEG | | | |
| 1 | 0.01 | 3.1 | 0.03 | 38.0 | 105 | 421.5 | 5.2 |
| 2 | 0.03 | 6.7 | 0.1 | 37.5 | 80 | 296.2 | 6.6 |
| 3 | 0.1 | 10.3 | 0.2 | 36.6 | 60 | 223.9 | 8.8 |
| 4 | 0.1 | 12.5 | 0.2 | 32.9 | 48 | 168.3 | 18.0 |
| 5 | 0.2 | 17.0 | 0.4 | 30.1 | 37 | 112.9 | 25.1 |
| 6 | 0.3 | 22.0 | 0.6 | 30.6 | 35 | 81.5 | 23.8 |

After 6 hours the mole ratio of EETB/TBM produced was 35 at 24% conversion of diethylene glycol.

Example 9

107.0 g of tertiary butyl amine and 75.6 g of diethylene glycol (2:1 mole ratio) was charged to an autoclave at room temperature under nitrogen. The catalyst was the catalyst of Example 7, re-activated at 200° C., 1 psi of hydrogen at 50 cc/min flow rate for 18 hours in-situ and having about 14% reduced nickel metal based on the whole reduced catalyst. Reactor temperature was held at 200° C. with stirring at 1800 rpm for 8 hours with GC sampling at the times indicated. Total reactor pressure was 385 psig. Initial hydrogen pressure at room temperature was 100 psig. The results are presented below:

Results of Example 9.

| Time (h) | Products (GC Weight %) | | | | EETB/TBM mole ratio | EETB/Bis-SE mole ratio | % Conversion Based on DEG |
|---|---|---|---|---|---|---|---|
| | Bis-SE | EETB | TBM | DEG | | | |
| 0.75 | 0.02 | 9.8 | 0.05 | 30.5 | 184 | 612.0 | 23.9 |
| 2 | 0.1 | 12.3 | 0.1 | 31.4 | 83 | 257.6 | 21.6 |
| 3 | 0.2 | 20.1 | 0.3 | 29.1 | 56 | 144.4 | 27.5 |
| 4.4 | 0.4 | 26.1 | 0.8 | 22.0 | 30 | 84.3 | 45.2 |
| 5.6 | 0.9 | 37.2 | 1.2 | 23.3 | 28 | 57.8 | 41.8 |
| 6 | 0.8 | 31.6 | 1.5 | 16.9 | 19 | 50.9 | 57.9 |
| 8 | 1.4 | 38.3 | 2.3 | 15.0 | 15 | 36.1 | 62.5 |

After 6 hours at 200° C. the mole ratio of EETB/TBM was 19 at 57.9% DEG conversion. Operation at the higher temperature significantly increased DEG conversion. It even achieved a higher EETB/FBM ratio at substantially similar DEG conversion levels, see: EETB/TBA of 56 at 27.5% DEG conversion after 3 hours versus EETB/TBA of 37 at 25% DEG conversion after 5 hours for the run at 180° C.

Example 10a

Preparation of 19.5% Ni on MCM-41/Alumina Bound without TEA Additive in the Solution 5.0 g of alumina bound MCM-41 extrudate support (whereby MCM-41 is an ordered siliceous mesoporous material and alumina is the matrix) was impregnated to the incipient wetness point with solution prepared by dissolving 6.44 g of nickel nitrate hexahydrate in 2.10 g of water. The sample was then dried in air at 60° C. for 2 hours and at 100° C. for 2 hours. The dried sample was calcined in flowing air by gradually ramping the temperature in the following protocol: 1° C./minute to 205° C. and hold for two hours, 1° C./minute to 300° C. and hold for two hours. The catalyst was reduced at 400° C. in flowing hydrogen for 1 hour (200 cc/min $H_2$ and 50 cc/min $N_2$) using the previously recited protocol. The so reduced catalyst was passivated to permit aerobic transfer to the autoclave for testing. Passivation was accomplished by cooling the reduced catalyst to room temperature under hydrogen flow. When cooled, the hydrogen was replaced by nitrogen and the catalyst was purged in nitrogen for an hour and gradually exposed to increasing concentrations of oxygen in nitrogen diluent. First, 0.02% oxygen in nitrogen was used for 30 minutes, followed by 0.1% oxygen in nitrogen for 30 minutes, followed by 0.3% oxygen in nitrogen for 30 minutes, followed by 10% oxygen in nitrogen for 30 minutes and finally followed by 20% oxygen in nitrogen for 30 minutes.

Example 10b 107.8 g of TBA and 78.0 g of DEG (2:1 molar ratio) were charged to an autoclave at room temperature under nitrogen. 1.60 g of the catalyst of Example 10(a) was reactivated at 200° C./1 psi of $H_2$ flow at 50 cc/min for 18 hours in the reactor before the addition of the TBA/DEG mixture. The catalyst had about 17% reduced nickel metal based on the whole reduced catalyst. Starting hydrogen pressure at room temperature was 100 psig. The reactor contents were stirred at 1800 rpm and heated at 200° C. for 8 hours with GC sampling every hour. The results are presented below:

| | Ni on MCM-41/alumina bound AM02 30-2 (without TEA additive) | | | | | | |
|---|---|---|---|---|---|---|---|
| Fraction # | Time (hrs) | Pressure (psig) | DEG Conv (%) | EETB/TBM (wt) | EETB/TBM (molar) | EETB/Bis SE (wt) | EETB/Bis SE (molar) |
| 52-1 | 1 | 383 | 2.1 | 101.3 | 90 | | |
| 52-2 | 2 | 370 | 5.8 | 87.8 | 78 | 1.3 | 1.7 |
| 52-3 | 3 | 372 | 8.5 | 81.6 | 72 | 2.3 | 3.0 |
| 52-4 | 4 | 370 | 15.3 | 69.8 | 62 | 2.0 | 2.7 |
| 52-5 | 5 | 369 | 15.0 | 66.5 | 59 | 2.0 | 2.6 |
| 52-6 | 8 | 364 | 18.5 | 57.3 | 51 | 1.6 | 2.2 |

Example 11

Utility of Other Amine and Glycol Starting Materials (2:1 Mole Ratio)

(a) 110.0 g of TBA and 92.2 g of dipropylene glycol were charged to an autoclave reactor under nitrogen at room temperature. 1.62 g of fresh nickel loaded catalyst of Example 1(b) was charged as received from the supplier to the reactor. Initial hydrogen pressure at room temperature was 100 psig. Total reactor pressure at reaction temperature was 287 psig. The reactor contents were heated at 180° C. with stirring at 1800 rpm for 7 hours with GC sampling every hour. In this and the following Examples 11(b)-(e) as previously stated above, it is believed the reduced metal content of this catalyst is about 42% based on the whole catalyst, the reduction occurring in-situ during the process step conducted at 180° C. in hydrogen. The results, in terms of glycol conversion and the ratio of amine alcohol product to all other products and by-products, are reported below.

| DPG and TBA (180° C., 2:1 TBA/DPG, 100 psig of $H_2$) | | | |
|---|---|---|---|
| Fraction # | Time (hrs) | DPG Conv (%) | PTB/All By-Product (wt) |
| 48-2 | 1 | 10.5 | 3.8 |
| 48-3 | 2 | 0.3 | 5.4 |
| 48-4 | 3 | 9.8 | 6.8 |
| 48-5 | 4 | 14.1 | 6.9 |
| 48-6 | 5 | 17.6 | 4.4 |
| 48-7 | 6 | 22.7 | 4.2 |
| 48-8 | 7 | 23.2 | 3.9 |

(b) 131.0 g of TBA and 68.0 g of propylene glycol (2:1 mole ratio) were charged to an autoclave reactor under nitrogen at room temperature. 1.59 g of fresh nickel loaded catalyst of Example 1(b) was charged as received from the supplier to the reactor. Initial hydrogen pressure at room temperature was 100 psig. Heating was at 180° C. wit stirring at 1800 rpm for 6 hours with GC sampling every hour. Total reactor pressure at reaction temperature was 325 psig. The results, in terms of glycol conversion and the ratio of amine alcohol product to all other products and by-products, are reported below.

| MPG and TBA (180° C., 2:1 TBA/MPG, 100 psig of $H_2$) | | | |
|---|---|---|---|
| Fraction # | Time (hrs) | MPG Conv (%) | PTB/All By-Product (wt) |
| 49-2 | 1 | 20.6 | 6.2 |
| 49-3 | 2 | 30.6 | 9.5 |
| 49-4 | 3 | 38.9 | 10.5 |
| 49-5 | 5 | 54.2 | 12.1 |
| 49-6 | 6 | 60.0 | 12.3 |

(c) 102.2 g TBA and 105.0 g triethylene glycol (2:1 mole ratio) were charged to an autoclave reactor under nitrogen at room temperature. 1.66 g of the nickel loaded catalyst of Example 1(b) was charged as received from the supplier to the reactor. Initial hydrogen pressure was 100 psig. Heating was at 180° C. for 6 hours with GC sampling every hour. Reactor contents were stirred at 1800 rpm. Total reactor pressure at reaction temperature was 275° C. The results, in terms of glycol conversion and the ratio of amine alcohol product to all other products and by-products, are reported below.

TEG and TBA (180° C., 2:1 TBA/TEG, 100 psig of $H_2$)

| Fraction # | Time (hours) | MPG Conv (%) | EETB/All By-Product (wt) |
|---|---|---|---|
| 50-2 | 1 | 14.4 | 13.0 |
| 50-3 | 2 | 23.2 | 14.3 |
| 50-4 | 3 | 29.9 | 22.0 |
| 50-5 | 4 | 44.1 | 25.1 |
| 50-6 | 5 | 55.7 | 24.4 |
| 50-7 | 6 | 63.3 | 24.5 |

(d) 99.1 g of isopropyl amine and 89.0 g of diethylene glycol (2:1 mole ratio) were charged to an autoclave reactor under nitrogen at room temperature. 1.62 g of fresh nickel loaded catalyst of Example 1b) was charged as received from the supplier to the reactor. Initial hydrogen pressure at room temperature was 100 psig. Heating was at 180° C. with stirring at 1800 rpm for 7 hours with GC sampling every hour. Total reactor pressure at reaction temperature was 436 psig. The results are presented below.

(180° C., 2:1 Isopropylamine and DEG) (100 psig of $H_2$)

| Fraction # | Time (hrs) | Pressure (psi) | DEG Conv (%) | EEIP/All By-Product (wt) |
|---|---|---|---|---|
| 55-1 | 0 | 436 | 48.11 | |
| 55-2 | 1 | 435 | 4.37 | 11.59 |
| 55-3 | 2 | 412 | 8.75 | 0.53 |
| 55-4 | 3 | 404 | 7.55 | 1.07 |
| 55-5 | 4 | 393 | 17.90 | 1.01 |
| 55-6 | 5 | 387 | 13.23 | 1.20 |
| 55-7 | 6 | 380 | 25.39 | 1.02 |
| 55-8 | 7 | 372 | 20.10 | 1.13 | e) 88.0 g of isopropylamine and 100.0 g of dipropylene glycol (2:1 mole ratio) were charged to an autoclave reactor under nitrogen at room temperature. 1.62 g of the nickel loaded catalyst of Example 1(b) was charged as received from the supplier to the reactor. Initial hydrogen pressure was 100 psig. Heating was at 180° C. for 6 hours with GC sampling every hour. Reactor contents were stirred at 1800 rpm. Total reactor pressure at reaction temperature was 405 psig. The results are presented below.

(180° C., 2:1 Isopropylamine and DPG)

| Fraction # | Time (hrs) | Pressure (psi) | DPG Conv (%) | PPIP/All By-Product (wt) |
|---|---|---|---|---|
| 56-2 | 1 | 388 | −4.34 | 0.13 |
| 56-3 | 2 | 378 | −2.95 | 0.22 |
| 56-4 | 3 | 372 | −3.34 | 0.32 |
| 56-5 | 4 | 370 | 5.91 | 0.30 |
| 56-6 | 5 | 365 | 4.26 | 0.35 |

Example 12

(a) 110.8 g of TBA and 78.4 g of DEG (2:1 mole ratio) were added to an autoclave under nitrogen at room temperature. 0.47 g of fresh nickel loaded catalyst of Example 1(b) (used as received from the supplier) was employed in the autoclave, a catalyst loading level of about 0.24 wt %. Starting hydrogen pressure at room temperature was 100 psia. Heating was to 200° C. with stirring at 1800 rpm for 8 hours with GC sampling every hour. Total reactor pressure at 200° C. was 347 psig. Based upon reduction experiments done on two different batches of this catalyst at 200° C. for 1 hour in hydrogen, it is believed the reduced metal content is about 40 to 43% based on the whole reduced catalyst. In this case the reduction would be occurring in situ during the process step. The results are presented below:

200° C. (100 psig of $H_2$, 2:1 TBA/DEG), unactivated

| | | | | | % Product after eliminating TBA | | |
|---|---|---|---|---|---|---|---|
| Fraction # | Time (hrs) | DEG Conv. (%) | EETB/TBM (wt) | EETB/BIS-SE (wt) | EETB | TBM | DEG |
| 170-1 | 1 | 11.8 | 149.4 | na | 16.0 | 0.1 | 82.6 |
| 170-2 | 2 | 6.3 | 117.5 | na | 21.5 | 0.2 | 77.1 |
| 170-3 | 3 | 21.0 | 58.2 | 219.4 | 32.6 | 0.6 | 64.8 |
| 170-4 | 4 | 26.8 | 41.4 | 129.3 | 39.2 | 0.9 | 57.1 |
| 170-5 | 5 | 32.8 | 32.7 | 99.2 | 44.6 | 1.4 | 50.8 |
| 170-6 | 6 | 40.2 | 25.7 | 68.6 | 50.8 | 2.0 | 43.5 |
| 170-7 | 7 | 45.3 | 20.7 | 54.9 | 54.5 | 2.6 | 38.5 |
| 170-8 | 8 | 51.9 | 15.8 | 43.4 | 56.5 | 3.6 | 33.4 |

(b) 110.8 g of TBA and 78.4 g DEG (2:1 mole ratio) were added to an autoclave under nitrogen at room temperature. 0.56 g of fresh nickel loaded catalyst of Example 1(b) (used as received from the supplier) was employed in the autoclave (a catalyst loading level of about 0.30 wt %). Starting hydrogen pressure at room temperature was 100 psig. Heating was to 200° C. with stirring at 1800 rpm for 7 hours with GC sampling every hour. Total reactor pressure at 200° C. was 347 psig. As in 12(a) it is believed the reduced metal content of the catalyst is about 40 to 43% based on the whole reduced catalyst. The results are presented below:

200° C. (100 psig of $H_2$, 2:1 TBA/DEG) unactivated

| Fraction # | Time (hrs) | DEG Conv. (%) | EETB/TBM (wt) | EETB/BIS-SE (wt) | % Product after eliminating TBA ||| 
|---|---|---|---|---|---|---|---|
| | | | | | EETB | TBM | DEG |
| 171-1 | 1 | 10.7 | 95.5 | na | 17.6 | 0.2 | 81.0 |
| 171-2 | 2 | 17.5 | 72.1 | na | 25.0 | 0.3 | 73.0 |
| 171-3 | 3 | 29.3 | 44.4 | 133.4 | 36.7 | 0.8 | 59.8 |
| 171-4 | 4 | 36.6 | 32.2 | 88.0 | 45.3 | 1.4 | 49.5 |
| 171-5 | 5 | 44.8 | 24.2 | 54.0 | 53.4 | 2.2 | 39.5 |
| 171-6 | 6 | 51.7 | 17.5 | 45.0 | 56.3 | 3.2 | 34.1 |
| 171-7 | 7 | 57.6 | 13.6 | 36.0 | 58.5 | 4.3 | 29.4 | c) 110.8 g of TBA and 78.4 g DEG (2:1 mole ratio) were added to an autoclave under nitrogen at room temperature. 0.47 g of fresh nickel loaded catalyst of Example 1(b) (used as received from the supplier) was employed in the autoclave (a catalyst loading level of about 0.25 wt %). Starting hydrogen pressure at room temperature was 100 psig. Heating was to 210° C. with stirring at 1800 rpm for 7 hours with GC sampling every hour. Total reactor pressure at 210° C. was 347 psig. As indicated previously, it is believed the reduced metal content of the catalyst is about 40 to 43% based on the whole reduced catalyst. The results are presented below:

210° C. (100 psig of $H_2$, 2:1 TBA/DEG) unactivated

| Fraction # | Time (hrs) | DEG Conv. (%) | EETB/TBM (wt) | EETB/BIS-SE (wt) | % Product after eliminating TBA ||| 
|---|---|---|---|---|---|---|---|
| | | | | | EETB | TBM | DEG |
| 172-1 | 1 | 13.7 | 75.1 | 295.7 | 20.0 | 0.3 | 78.6 |
| 172-2 | 2 | 22.7 | 45.8 | 175.7 | 28.3 | 0.6 | 69.4 |
| 172-3 | 3 | 31.5 | 31.3 | 91.4 | 40.6 | 1.3 | 55.1 |
| 172-4 | 4.05 | 44.1 | 20.6 | 63.5 | 47.9 | 2.3 | 45.3 |
| 172-5 | 5 | 49.1 | 17.4 | 41.8 | 55.6 | 3.2 | 37.0 |
| 172-6 | 6 | 55.1 | 12.9 | 37.7 | 56.2 | 4.3 | 32.0 |
| 172-7 | 7 | 59.7 | 11.5 | 28.2 | 59.3 | 5.2 | 26.3 |

(d) 110.8 g of TBA and 78.4 g of DEG (2.1 mole ratio) were added to an autoclave under nitrogen at room temperature. 0.76 g of fresh nickel loaded catalyst of Example 1(b) (used as received from the supplier) was employed in the autoclave (a catalyst loading level of about 0.40 wt %). Starting hydrogen pressure at room temperature was 100 psig. Heating was to 200° C. with stirring at 1800 rpm for 7 hours with GC sampling every hour. Total reactor pressure at 200° C. was 335 psig. As indicated previously, it is believed the reduced metal content of the catalyst is about 40 to 43% based on the whole reduced catalyst.

The results are presented below:

200° C. (100 psig of H$_2$, 2:1 TBA/DEG) unactivated

| Fraction # | Time (hrs) | DEG Conv. (%) | EETB/TBM (wt) | EETB/BIS-SE (wt) | % Product after eliminating TBA | | |
|---|---|---|---|---|---|---|---|
| | | | | | EETB | TBM | DEG |
| 174-1 | 1 | 13.0 | 117.7 | na | 21.3 | 0.2 | 77.4 |
| 174-2 | 2 | 24.0 | 71.5 | na | 28.1 | 0.4 | 69.6 |
| 174-3 | 3 | 33.5 | 37.6 | 114.3 | 40.9 | 1.1 | 54.7 |
| 174-4 | 4 | 38.6 | 27.8 | 78.4 | 48.6 | 1.8 | 45.5 |
| 174-5 | 5 | 49.9 | 18.9 | 45.0 | 56.6 | 3.0 | 34.2 |
| 174-6 | 6 | 57.9 | 13.6 | 35.5 | 59.2 | 4.4 | 28.6 |
| 174-7 | 7 | 65.5 | 10.2 | 27.8 | 60.3 | 5.9 | 23.5 |

The results of Experiment 2 which had a catalyst loading level of about 0.86 wt % are repeated here but to also report the % product after eliminating TBA.

| Fraction # | Time (hrs) | DEG Conv. (%) | EETB/TBM (wt) | EETB/BIS-SE (wt) | % Product after eliminating TBA | | |
|---|---|---|---|---|---|---|---|
| | | | | | EETB | TBM | DEG |
| 30-1 | 1 | 21.0 | 79.0 | 135.7 | 38.5 | 0.5 | 57.4 |
| 30-2 | 2 | 57.0 | 21.8 | 46.2 | 55.0 | 2.5 | 34.8 |
| 30-3 | 3 | 68.7 | 12.4 | 22.8 | 59.9 | 4.8 | 20.0 |
| 30-4 | 4 | 78.8 | 7.8 | 14.0 | 59.8 | 7.7 | 12.2 |
| 30-5 | 5 | 87.0 | 4.8 | 9.6 | 54.4 | 11.2 | 7.8 |
| 30-6 | 6 | 91.9 | 3.7 | 7.2 | 50.1 | 13.6 | 5.5 |

Figure 5:
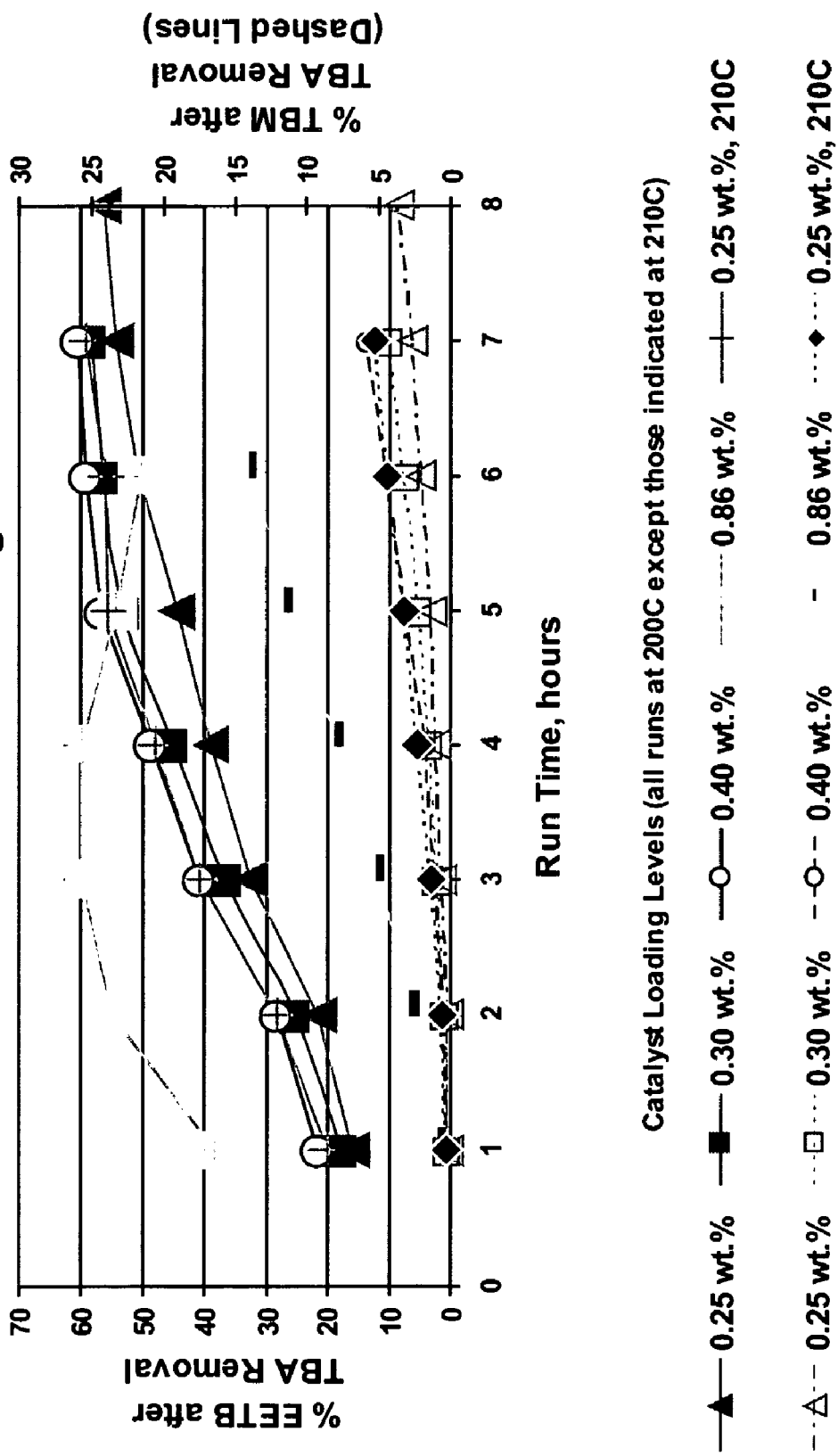
FIG. 5 is a plot of the effect of different catalyst loading levels on the synthesis of EETB at 200° C. and 210° C.

The data of % EETB after TBA removal and % TBM after TBA removal are plotted in FIG. 5. It is seen that the reaction proceeds at very low catalyst loading levels, levels of about 0.4 to 0.25 wt % providing about the same level of EETB production (albeit over a longer time) but at lower overall TBM production as compared against Example 2 which employed a catalyst loading level of about 0.86 wt %.

push the reaction in favor of products. Starting hydrogen pressure at room temperature was 100 psig. Heating was to 200° C. with stirring at 1800 rpm for 10 hours with GC sampling at the times reported below. Total reactor pressure at 200° C. was 343 psig. As in Example 12(a) it is believed the reduced metal content of the catalyst is about 40 to 43% based on the whole reduced catalyst. The results are presented below:

200° C. (100 psig of H$_2$, 2:1 TBA/DEG) unactivated

| Fraction # | Time (hrs) | DEG Conv. (%) | EETB/TBM (wt) | EETB/BIS-SE (wt) | % Product after eliminating TBA | | |
|---|---|---|---|---|---|---|---|
| | | | | | EETB | TBM | DEG |
| 175-1 | 2 | 23.2 | 77.5 | na | 25.8 | 0.3 | 72.7 |
| 175-2 | 3 | 31.5 | 60.3 | 265.0 | 32.6 | 0.5 | 64.5 |
| 175-3 | 4 | 31.4 | 46.9 | 181.0 | 41.1 | 0.9 | 55.0 |
| 175-4 | 6 | 45.3 | 25.6 | 88.0 | 53.2 | 2.1 | 39.1 |
| 175-6 | 8 | 67.0 | 10.7 | 40.6 | 63.2 | 4.4 | 20.8 |
| 175-7 | 9 | 64.2 | 12.3 | 35.3 | 66.3 | 5.4 | 19.4 |
| 175-8 | 10 | 72.1 | 7.9 | 27.4 | 64.0 | 8.1 | 15.8 |

Example 13

110.8 g of TBA and 78.4 g of DEG (2:1 mole ratio) were added to an autoclave under nitrogen at room temperatures. 0.47 g of fresh nickel loaded catalyst of Example 1(b) (used as received from the supplier was employed in the autoclave, a catalyst loading level of about 0.25 wt % based on the reactant charge. 26.8 g MgO was also added to the autoclave to see if converting the water produced during the reaction would As can be seen by comparing the % EETB produced in Example 13 versus the % EETB produced in Example 12(a), the presence of the MgO which reacts with water to produce magnesium hydroxide pushes the reaction to produce more of the desirable ETB product, compare EETB yields at 8 hours in each example. In Example 12 the EETB yield at 8 hours was 56.5% while in Example 13 the EETB yield at 8 hours was 63.2%.

COMPARATIVE EXAMPLES

Comparative Example A

E-480P is a nickel catalyst containing about 65% nickel deposited on a support. It has an average particle diameter of 9 μm, and an apparent bulk density of 20 lbs/ft$^3$.

Comparative Example B

EETB synthesis procedures similar to those used in Example 1 were employed. E-480P (Comparative Example A) was evaluated at 180° C. This catalyst was reactivated before use at 200° C., 1 psi of H$_2$ at 50 cc/min for 19 hours resulting in a metallic reduced nickel content of 53% based on the whole reduced catalyst. 108 g of TBA and 76.4 g of DEG were charged to an autoclave under nitrogen at room temperature. 1.59 g of catalyst was added. Initial hydrogen pressure at room temperature was 100 psig. The autoclave was heated to 180° C. and the content stirred at 1800 rpm. Total vessel pressure was 262 psig. Results are presented below.

Results of Comparative Example B (180° C.)

| Time | Products (GC Weight %) | | | | EETB/TBM | EETB/Bis-SE | % Conversion |
|---|---|---|---|---|---|---|---|
| (h) | Bis-SE | EETB | TBM | DEG | mole ratio | mole ratio | Based on DEG |
| 1 | 0.04 | 5.4 | 0.1 | 41.2 | 74 | 193.5 | −2.7 |
| 2 | 0.05 | 10.6 | 0.2 | 40.7 | 61 | 293.8 | −1.5 |
| 3 | 0.1 | 13.5 | 0.3 | 34.4 | 42 | 142.0 | 14.3 |
| 4 | 0.2 | 18.8 | 0.6 | 28.9 | 28 | 104.9 | 27.9 |
| 6 | 0.5 | 27.5 | 1.5 | 26.1 | 17 | 80.1 | 34.9 |

Comparative Example C

A fresh sample of catalyst from Comparative Example A, E-480P, was employed and used as received, no reactivation step was practiced. Earlier work had shown that this commercial catalyst performed similarly whether reactivated or used as received. About 107 g of TBA and 76.2 g of DEG were charged to an autoclave under nitrogen at room temperature. 1.59 g catalyst was added. Initial hydrogen pressure at room temperature was 100 psig. The autoclave was heated to 200° C. Total vessel pressure was 385 psig. Autoclave contents were stirred at 1800 rpm. Based on reduction experiments done on this catalyst at 200° C. for 1 hour in hydrogen, it is believed that in the course of use in the process run at 200° C. in hydrogen, the reduced metal content is believed to be about 47-48% nickel based on the whole reduced catalyst. Results are presented below.

Results of Comparative Example C (200° C.)

| Time | Products (GC Weight %) | | | | EETB/TBM | EETB/Bis-SE | % Conversion |
|---|---|---|---|---|---|---|---|
| (h) | Bis-SE | EETB | TBM | DEG | mole ratio | mole ratio | Based on DEG |
| 1 | 0 | 2.8 | 0.02 | 43.3 | 120 | | −7.5 |
| 2 | 0.02 | 7.3 | 0.06 | 51.5 | 102 | 434.8 | −28.3 |
| 3 | 0.05 | 10.8 | 0.1 | 47.9 | 78 | 320.3 | −19.5 |
| 4 | 0.1 | 16.5 | 0.3 | 44.2 | 53 | 226.2 | −10 |
| 5 | 0.2 | 22.5 | 0.6 | 36.5 | 34 | 153.0 | 9.1 |
| 6 | 0.3 | 27.0 | 1.0 | 31.3 | 25 | 115.8 | 21.9 |
| 7 | 0.4 | 27.1 | 1.2 | 25.6 | 19 | 98.5 | 36.1 |

Comparative Example D 1.14 g of E-480P (Comparative Example A) was employed to synthesize EETB. The catalyst was used as received and did not undergo any reactivation. 66.0 g of tertiary-butyl amine, 47.9 g of diethylene glycol, and 119.0 grams of toluene (as inert solvent) were then charged to the reactor under nitrogen at room temperature. The autoclave was charged at room temperature with 100 psig of hydrogen. The contents of the autoclave reactor were then heated to 200° C. for 6 hours. Based on reduction experiments done on this catalyst at 200° C. for 1 hour, it is believed the reduced metal content is about 47-48% based on the whole catalyst, see Comparative Example C. The pressure at 200° C. was 310 psig. The final reactor product was analyzed by NMR. The results are presented below.

Results of Comparative Example D

| Time | Products (¹H NMR) | | | EETB/TBM | % Conversion |
|---|---|---|---|---|---|
| (h) | EETB | TBM | DEG | Mole ratio | Based on DEG |
| 6 | 50 | 6 | 44 | 8 | 56 |

Comparative Example E

Ni-5132P is a nickel catalyst containing about 60% nickel deposited on a support. It has a surface area of about 160 $m^2/g$, an average particle size of about 6 μm and a pore volume of about 0.00508 ml/g.

Comparative Example F 1.11 g of Ni-5132P (Comparative Example E) was employed to synthesize EETB. The catalyst was used as received. 66.0 g of tertiary-butyl amine, 47.9 g of diethylene glycol, and 119.0 grams of toluene (as inert solvent) were then charged to the reactor under nitrogen at room temperature. The autoclave was charged at room temperature with 100 psig of hydrogen. The contents of the autoclave reactor were then heated to 200° C. for 6 hours. Based on reduction experiments done on this catalyst at 200° C. for 1 hour in hydrogen, it is believed the reduced metal content is about 52% based on the whole reduced catalyst. The pressure at 200° C. was 290 psig. The final reactor product was analyzed by NMR. The results are presented below.

Results of Comparative Example F

| Time | Products (¹H NMR) | | | EETB/TBM | % Conversion |
|---|---|---|---|---|---|
| (h) | EETB | TBM | DEG | Mole ratio | Based on DEG |
| 6 | 72 | 15 | 13 | 5 | 87 |

Comparative Example G 109.5 g of TBA and 77.4 g of DEG (2:1 molar ratio) were charged to an autoclave at room temperature under nitrogen. 1.61 g Ni-5132P (Catalyst of Comparative Examples E and F) was charged as received from the supplier to the reactor. Initial hydrogen pressure at room temperature was 100 psig. Reactor contents were stirred at 1800 RPM. Reactor contents were heated at 200° C. with stirring at 1800 rpm for 4 hours with GC sampling every hour. Total reactor pressure at reaction temperature was 385 psig. Based upon reduction experiments done on this catalyst at 200° C. for 1 hour in hydrogen, it is believed the reduced nickel metal content is about 52% based on the whole reduced catalyst. The results are presented below:

| | | | Ni-5132P at 200° C. | | | |
|---|---|---|---|---|---|---|
| Fraction # | Time (hrs) | DEG Conv (%) | EETB/TBM (wt) | EETB/TBM (molar) | EETB/Bis SE (wt) | EETB/Bis SE (molar) |
| 51-1 | 1 | 18.8 | 57.6 | 51 | 1.1 | 1.5 |
| 51-2 | 2 | 45.1 | 25.7 | 23 | 0.8 | 1.1 |
| 51-3 | 3 | 53.0 | 16.8 | 15 | 0.7 | 0.9 |
| 51-4 | 4 | 65.1 | 11.0 | 10 | 0.7 | 0.9 |

Comparative Example H

The process of Example 8 was repeated, but in this instance the catalyst, Ni MCM-41/alumina bound was not subjected to a 400° C. activation in hydrogen followed by passivation. Rather, the catalyst was subjected simply to a 200° C. activation step resulting in about 9.0% reduced nickel metal based on the whole catalyst. The example exhibited minimal DEG conversion and an unmeasurably small EETB production, showing that activation at a temperature high enough to secure a reduced nickel catalyst having at least 10% reduced metal based on the whole catalyst is preferred.

Figure 3:
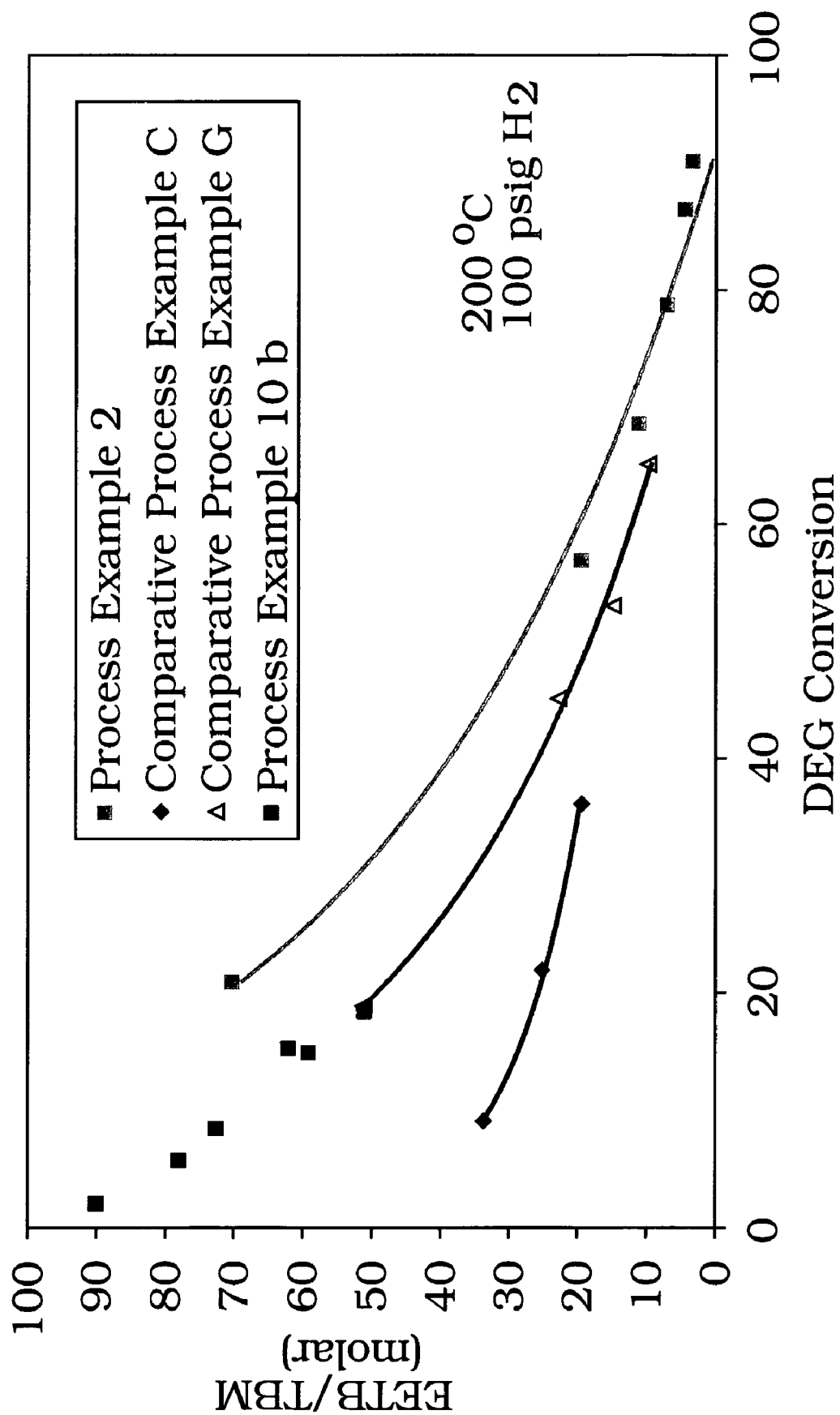
FIG. 3 is a plot of the level of DEG conversion versus EETB/TBM ratio for four runs comparing four catalysts under substantially equivalent conditions. The catalysts evaluated were a commercial catalyst within the scope of the invention, E 480-P, Ni-5132, and Ni on MCM-41/alumina bound made without a dispersion aid.

FIG. 3 compares the data for Example 10b, Comparative Examples C and G and Example 2. It would seem that the results for comparative Example G (Ni-5132) and Example 10b Ni MCM-41/alumina bound (no TEA dispersant) appear to follow the same curve until the difference in catalyst metal loading is taken into consideration. The catalyst of Comparative Example G (Ni-5132) contains about 52% reduced nickel metal based on the whole reduced catalyst whereas catalyst of Example 10b contains only about 17% reduced nickel based on the whole reduced catalyst. Thus, the apparently equivalent performance under identical operating conditions is achieved in the case of catalyst of Example 10a at a metal loading level about 70% lower than that of Comparative Example G.

The catalyst of comparative process Example C (E-480P) is not only less active than the catalyst of process Examples 2 and 10(b), but its selectivity toward EETB is significantly lower at the higher DEG conversion levels than the catalyst described in process Example 2.

The differences between the catalysts in light of their physical characteristics are presented below:

|  | Ni/MCM-41/ alumina bound (w/disp) | E-480P | Ni-5132 | Commercial cat of Example 1(b) | Ni-MCM-41/ alumina bound w/o disp |
|---|---|---|---|---|---|
| BET Surface Area m²/g | 514.41 | 175.38 | 161.62 | 283.01 | 536.0 |
| Pore Volume cm³/g | 0.735 | 0.58 | 1.03 | 0.34 | .880 |
| Micropore Volume cm³/g | 0.241 | 0.014 | 0.0051 | 0.22 | 0.274 |

Figure 4:
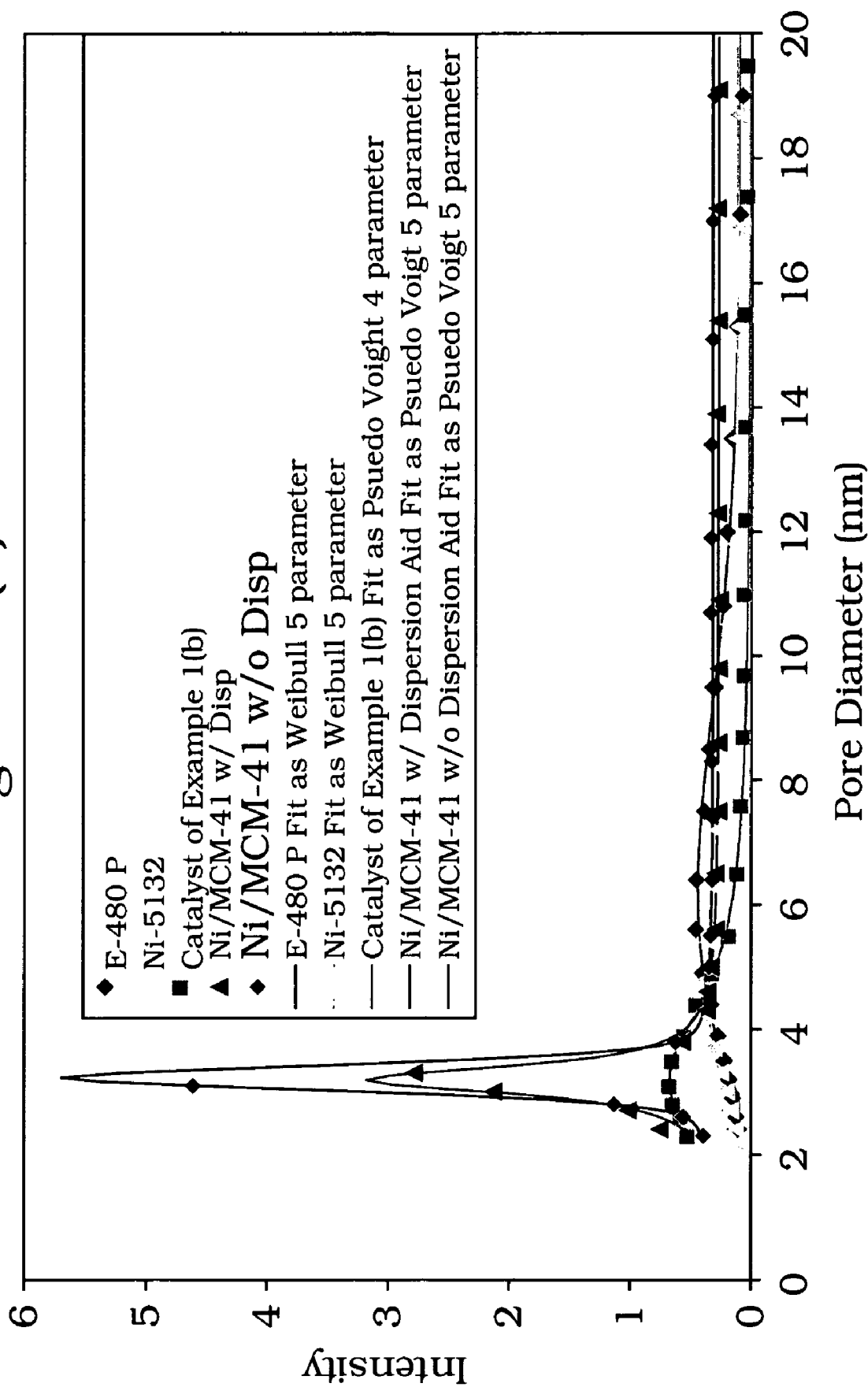
FIG. 4a is a plot of pore diameter against peak intensity as determined by nitrogen BJH adsorption using a peak fitting function to reproduce the line shape for the five catalysts.
FIG. 4b is a normalized signal representation of the plot of pore diameter versus normalized intensity for the same five catalysts, normalization of the area under each curve being achieved by dividing the area of each fraction (intensity multiplied by width) by the total area.
Figure 4:
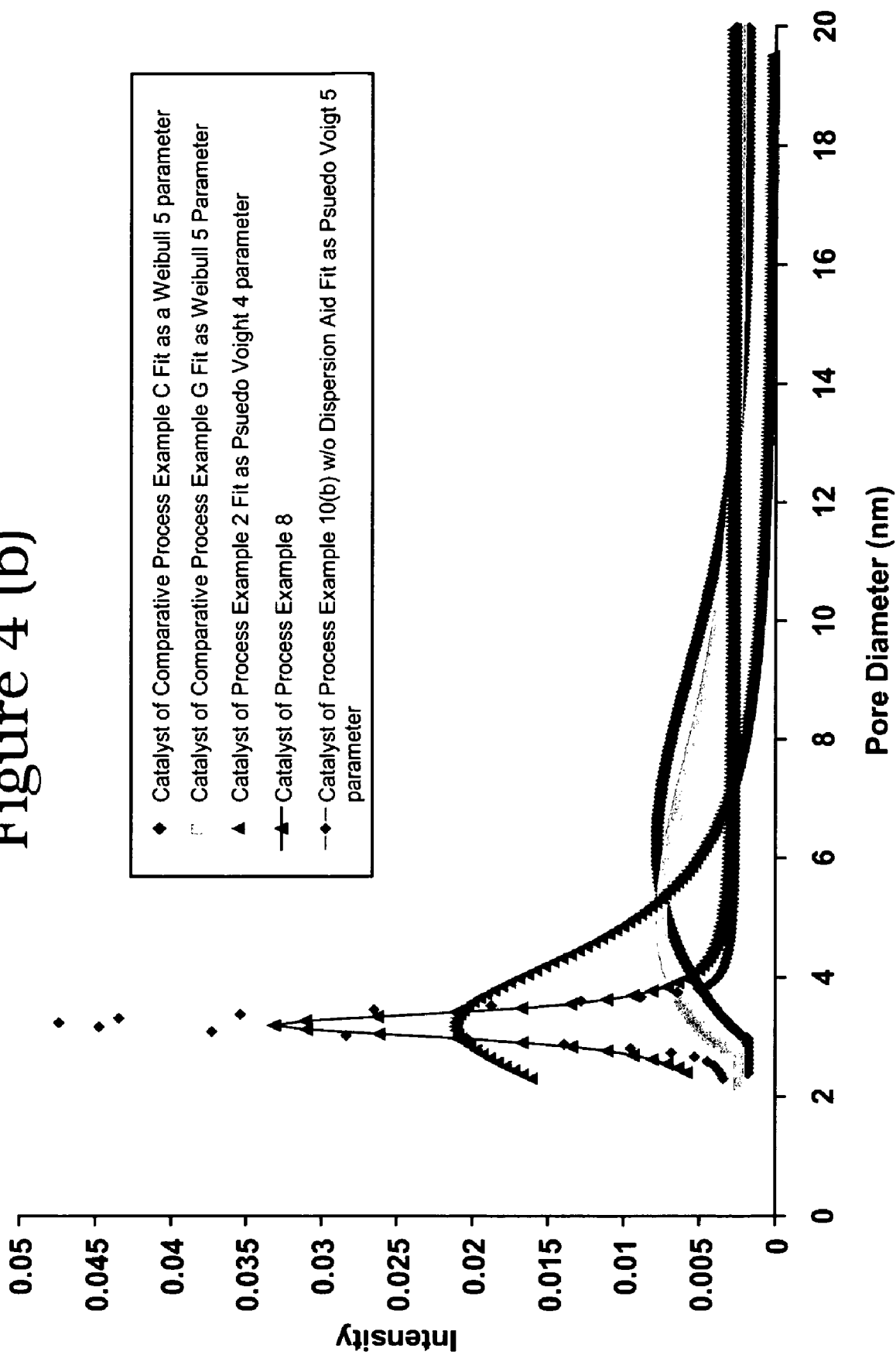

Nitrogen BJH adsorption data for each sample was obtained as average diameter (nm) versus dV/dlog(D) pore volume (cm³/g-nm). Because the data was not uniformly spaced along the x axis, each data set was individually fit using a peak fitting function to reproduce the line shape. The original data points are shown in the symbols in FIG. 4A, the fitted functions are shown in the lines. Using the fitted functions, the total area under each curve was determined up to 19.99 nm by multiplying the intensity of each fraction by its width (set to approximately 0.07 nm), and summing the values. The area under each curve was then normalized, by dividing the area of each fraction (against intensity times width) by the total area. The normalized curves are plotted in FIG. 4B. The contribution in each range was obtained by summing the normalized values over the desired range (e.g., 5.00 to 9.99 nm), as reported in the table below.

|  | E-480P | Ni-5132 | Commercial Cat of Example 1(b) | Ni/MCM-41/ alumina bound w/dispersion aid | Ni/MCM-41/ alumina bound w/o dispersion aid |
|---|---|---|---|---|---|
| Up to 4.99 nm | 16% | 22% | 69% | 40% | 44% |
| 5.00 nm to 9.99 nm | 48% | 41% | 24% | 20% | 19% |
| 10.00 nm to 14.99 nm | 22% | 20% | 5% | 20% | 18% |
| 15.00 to 19.99 nm | 14% | 17% | 2% | 20% | 19% |

E-180P Fit as Weibull 5 parameter
Ni-5132 Fit as Weibull 5 parameter
Commercial Cat of Example 1(b) Fit as Psuedo Voigt 4 parameter
Ni/MCM-41/alumina bound w/Dispersion Aid Fit as Psuedo Voigt 5 parameter
Ni/MCM-41/alumina bound w/o Dispersion Aid Fit as Psuedo Voigt 5 parameter The sharpness or broadness of the peak affects which type of peak fitting function will accurately reproduce the line shape. The fitting functions were determined by fitting the different functions and choosing the fit with the smallest residual values (difference in predicted fit and actual data points).

From this it is seen that the catalysts which exhibit unexpected superior performance in the present process are characterized by a high content of pores up to about 4.99 nm whereas the prior art catalysts which exhibit lesser performance have a low content of pores in the up to about 4.99 nm. Similarly, the catalysts which exhibit superior performance have micropore volume ranging from about 17 to about 50 times that of the prior art catalyst. It is unexpected that these differences would result in an improvement in the process for the production of severely sterically hindered amino ether alcohols from amines and glycols. The pore size distribution obtained for the MCM-41 based catalysts differ from that observed for the pure MCM-41 crystals, which exhibit the narrow pore size distribution typically described in the relevant literature. The distribution shown in the present examples is broadened due to the addition of the alumina binder and the high loading of nickel metal. The present catalyst shows a constant contribution to pores in the up to 19.99 nm range due to the non-zero baseline in this region.

It is clearly seen that catalysts marked by possessing the pore size distribution and micropore volume as recited herein constitute catalysts the use of which exhibit unexpected superior performance in the process for the synthesis of severely sterically hindered amine ether alcohols from amine/glycol mixtures.

The invention claimed is:

1. A process for the production of sterically hindered amino ether alcohols, diaminopolyalkenyl ethers, and mixtures thereof, comprising reacting an alkyl substituted primary amino compound with a polyalkenyl ether glycol, over a catalyst comprising a catalytically active metal, but excluding platinum and palladium, on a support, the support characterized by a micropore volume above about 0.5 cm³/g, the metal loaded catalyst exhibiting a pore size distribution when normalized for pore of 19.99 nm or less of about 30% or more of pores of up to 4.99 nm, the pores of 5 to up to 19.99 nm constituting the balance.

2. The process of claim 1 wherein the catalyst has a BET surface area of greater than 50 m²/g.

3. The process of claim 1 wherein the primary amine to glycol ratio is in the range of about 10:1 to 0.5:1.

4. The process of claim 1 wherein the primary amine compound is of the general formula $R^1$—$NH_2$ wherein $R^1$ is selected from the group consisting of secondary- and tertiary-alkyl radicals having 3 to 8 carbon atoms, cycloalkyl radicals having 3 to 8 carbon atoms, and mixtures thereof, and the polyalkenyl ether glycol is of the general formula

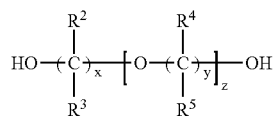

wherein $R^2$, $R^3$, $R^4$ and $R^5$ are each independently selected from the group consisting of hydrogen, C1-C4 alkyl radicals, and C3-C8 cycloalkyl radicals with the process that if the carbon atom of $R^1$ directly attached to the nitrogen atoms is a secondary alkyl radical, at least one of $R^2$ and $R^3$ directly bonded to the carbon which is bonded to the hydroxyl group is an alkyl or cycloalkyl radical, x and y are each positive integers independently ranging from 2 to 4, z is from 1 to 10 and the ratio of alkyl substituted primary amine to glycol is less than 2:1 when z is greater than 1.

5. The process of claim 1 wherein the initial hydrogen pressure at room temperature is from about zero to about 300 psig, the temperature is about 150° C. to about 350° C., total reactor pressure at operating temperature is from 50 to 1,500 psig, and reactor time is from 0.5 to 24 hours.

6. The process of claim 1 wherein the catalyst comprises about 2.5 to about 80% reduced metal based on the whole reduced catalyst.

7. The process of claim 1, 2, 3, 4, 5 or 6 wherein the catalytically active metal is nickel.

8. The process of claim 1, 2, 3, 4, 5 or 6 wherein the catalyst support comprises mesoporous materials wherein the mesoporous material is selected from the group comprising M41-S materials.

9. The process of claim 1, 2, 3, 4, 5 or 6 wherein the support material comprises MCM-41.

10. The process of claim 1 wherein the catalyst comprises at least about 10% reduced nickel based on the whole reduced catalyst deposited on a support and characterized by having a BET surface area above 50 $m^2/g$, a micropore volume above about 0.05 $cm^3/g$, the metal loaded catalyst exhibiting a pore size distribution, when normalized for pore of 19.99 nm and less of about 30% or more of pores of up to 4.99 nm, the pore of 5 to up to about 19.99 nm constituting the balance, the alkyl substituted primary amine is selected from the group consisting of isopropyl amine, tertiary-butyl amine, 1-methyl-1-ethyl propyl amine and tertiary-amyl amine, the glycol is selected from the group consisting of diethylene glycol, triethylene glycol, di-isopropylene glycol, the ratio of amine to glycol ranges from about 10:1 to 0.5:1, initial hydrogen pressure at room temperature ranges from zero to 300 psig, temperature range from about 150° C. to 350° C., total reactor pressure at operating temperature ranges from about 50 to 1,000 psig, and time ranges from about 0.5 to 24 hours.

11. The process of claim 10 wherein the primary amine is tertiary-butyl amine the polyalkenyl glycol is diethylene glycol, the ratio of amine to glycol ranges from about 3:1 to 1:1, the catalytically active metal is nickel present in an amount in the range of about 10 to about 65 wt % reduced nickel based on the whole reduced catalyst, temperature is in the range of about 160° C. to about 300° C., reaction time is in the range of about 1 to 12 hours, and the metal loaded catalyst has a pore size distribution of about 35-100% of pores of up to 4.99 nm, and pores of 5.0 to up to about 19.99 nm constituting the balance, when the pore size distribution is normalized for 19.99 nm and less.

12. The process of claim 1, 10 or 11 wherein the amount of catalyst present with respect to the total amount of reactant is in the range of from about 0.001 to about 10 wt % catalyst based on the weight of the total reactant charge.

13. The process of claim 10 or 11 wherein the catalyst support comprises mesoporous materials wherein the mesoporous material is selected from the group comprising M41-S materials.

14. The process of claim 13 wherein the support material comprises MCM-41.

* * * * *